US008441633B2

(12) United States Patent
Truong et al.

(10) Patent No.: US 8,441,633 B2
(45) Date of Patent: May 14, 2013

(54) MULTIPLE-PHOTON EXCITATION LIGHT SHEET ILLUMINATION MICROSCOPE

(75) Inventors: Thai V. Truong, Pasadena, CA (US); John M. Choi, Tujunga, CA (US); Scott E. Fraser, LaCanada, CA (US); Willy Supatto, Paris (FR); David S. Koos, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 125 days.

(21) Appl. No.: 12/915,921

(22) Filed: Oct. 29, 2010

(65) Prior Publication Data

US 2011/0122488 A1 May 26, 2011

Related U.S. Application Data

(60) Provisional application No. 61/256,010, filed on Oct. 29, 2009, provisional application No. 61/256,005, filed on Oct. 29, 2009.

(51) Int. Cl.
| | |
|---|---|
| *G01J 3/40* | (2006.01) |
| *G01J 3/30* | (2006.01) |
| *G01J 1/58* | (2006.01) |
| *F21V 9/16* | (2006.01) |
| *G01T 1/10* | (2006.01) |
| *G21H 3/02* | (2006.01) |
| *G21K 5/00* | (2006.01) |
| *H01J 65/06* | (2006.01) |
| *H01J 65/08* | (2006.01) |

(52) U.S. Cl.
USPC ...... 356/301; 356/317; 250/458.1; 250/459.1

(58) Field of Classification Search .................. 356/309, 356/320, 301, 317; 250/458.1, 459.1
See application file for complete search history.

(56) References Cited

U.S. PATENT DOCUMENTS 6,020,591 A * 2/2000 Harter et al. ............... 250/458.1
6,844,963 B2 * 1/2005 Iketaki et al. .................. 359/368
(Continued)

FOREIGN PATENT DOCUMENTS

DE 102007047461 A1 4/2009
EP 1207387 A1 5/2002
(Continued)

OTHER PUBLICATIONS

Volodymyr Nikolenko et al., SLM microscopy: scanless two-photon imaging and photostimulation with spatial light modulators, 2008, Frontiers in Neural Circuits, vol. 2, Article 5, pp. 1-14.*

(Continued)

*Primary Examiner* — Gregory J Toatley
*Assistant Examiner* — Shawn Decenzo
(74) *Attorney, Agent, or Firm* — Kauth, Pomeroy, Peck & Bailey LLP

(57) ABSTRACT

An apparatus for and method of performing multi-photon light sheet microscopy (MP-LISH), combining multi-photon excited fluorescence with the orthogonal illumination of light sheet microscopy are provided. With live imaging of whole *Drosophila* and zebrafish embryos, the high performance of MP-LISH compared to current state-of-the-art imaging techniques in maintaining good signal and high spatial resolution deep inside biological tissues (two times deeper than one-photon light sheet microscopy), in acquisition speed (more than one order of magnitude faster than conventional two-photon laser scanning microscopy), and in low phototoxicity are demonstrated. The inherent multi-modality of this new imaging technique is also demonstrated second harmonic generation light sheet microscopy to detect collagen in mouse tail tissue. Together, these properties create the potential for a wide range of applications for MP-LISH in 4D imaging of live biological systems.

26 Claims, 15 Drawing Sheets

U.S. PATENT DOCUMENTS

| | | | |
|---|---|---|---|
| 6,856,712 | B2 | 2/2005 | Fauver et al. |
| 7,282,716 | B2 | 10/2007 | Prelewitz et al. |
| 7,307,802 | B2 | 12/2007 | Unger |
| 7,787,179 | B2 | 8/2010 | Lippert et al. |
| 2006/0011804 | A1 | 1/2006 | Engelmann et al. |
| 2007/0087284 | A1* | 4/2007 | Fleming et al. ............... 430/269 |
| 2007/0109633 | A1* | 5/2007 | Stelzer ......................... 359/385 |
| 2007/0148760 | A1 | 6/2007 | Klesel et al. |
| 2008/0043786 | A1 | 2/2008 | Wilhelm et al. |
| 2008/0116392 | A1* | 5/2008 | Brooker ..................... 250/458.1 |
| 2009/0027769 | A1 | 1/2009 | Saito et al. |
| 2009/0028503 | A1 | 1/2009 | Garrett et al. |
| 2009/0225413 | A1 | 9/2009 | Stelzer et al. |
| 2010/0067102 | A1* | 3/2010 | Yokoi et al. .................. 359/385 |
| 2010/0075361 | A1 | 3/2010 | Mattoussi et al. |
| 2010/0276608 | A1 | 11/2010 | Liu et al. |
| 2010/0309548 | A1 | 12/2010 | Power et al. |
| 2011/0115895 | A1 | 5/2011 | Huisken |
| 2011/0134521 | A1 | 6/2011 | Truong et al. |
| 2012/0141981 | A1* | 6/2012 | Pantazis et al. ................ 435/6.1 |

FOREIGN PATENT DOCUMENTS

| | | |
|---|---|---|
| WO | 9107651 A1 | 5/1991 |
| WO | 2011059826 A2 | 5/2011 |
| WO | 2011059833 A2 | 5/2011 |
| WO | 2011059833 A3 | 5/2011 |
| WO | 2011059826 A3 | 9/2011 |

OTHER PUBLICATIONS

Bewersdorf et al., "Multifocal multiphoton microscopy", Optics Letters, May 1, 1998, vol. 23, No. 9, pp. 655-657.

Bousso, "Real-time imaging of T-cell development", Current Opinion in Immunology, 2004, vol. 16, pp. 400-405.

Breuninger et al., "Lateral modulation boosts image quality in single plane illumination fluorescence microscopy", Optics Letters, Jun. 1, 2007, vol. 32, No. 13, pp. 1938-1940.

Campagnola et al., "Second-harmonic imaging microscopy for visualizing biomolecular arrays in cells, tissues and organisms", Nature Biotechnology, Nov. 2003, vol. 21, No. 11, pp. 1356-1360.

Denk et al., "Two-Photon Laser Scanning Fluorescence Microscopy", Reports, Apr. 6, 1990, vol. 248, No. 4951, pp. 73-76.

Dodt et al., "Ultramicroscopy: three-dimensional visualization of neuronal networks in the whole mouse brain", Nature Methods, Apr. 2007, Vo. 4, No. 4, pp. 331-336.

Fahrbach et al., "Microscopy with self-reconstructing beams", Nature Photonics, Nov. 2010, vol. 4, pp. 780-785.

Friedl, "Immunological techniques Dynamic imaging of the immune system", Current Opinion in Immunology, 2004, vol. 16, pp. 389-393.

Fuchs et al.,, "Thin laser light sheet microscope for microbial oceanography", Optics Express, Jan. 28, 2002, vol. 10, No. 2, pp. 145-154.

Holekamp et al., "Fast Three-Dimensional Fluorescence Imaging of Activity in Neural Populations by Objective-Coupled Planar Illumination Microscopy", Neuron, Mar. 13, 2008, vol. 57, pp. 661-672.

Huisken et al., "Even fluorescent excitation by multidirectional selective plane illumination microscopy", Optics Letters, Sep. 1, 2007, vol. 32, No. 17, pp. 2608-2610.

Huisken et al., "Optical Sectioning Deep Inside Live Embryos by Selective Plane Illumination Microscopy", Science, 2004, vol. 305, pp. 1007-1009.

Huisken et al., "Selective plane illumination microscopy techniques in developmental biology", Development, 2009, vol. 136, pp. 1963-1975.

Ji et al., "Adaptive optics via pupil segmentation for high-resolution imaging in biological tissues", Nature Methods, Feb. 2010, vol. 7, No. 2, pp. 141-150.

Ji et al., "Advances in the speed and resolution of light microscopy", Current Opinion in Neurobiology, 2008, vol. 18, pp. 605-616.

Ji et al., "High-speed, low-photodamage nonlinear imaging using passive pulse splitters", Nature Methods, Feb. 2008, vol. 5, No. 2, pp. 197-202.

Keller et al., "Fast, high-contrast imaging of animal development with scanned light sheet-based structured-illumination microscopy", Nature Methods, Advance Online Publication, Jul. 4, 2010, pp. 1-9.

Keller et al., "Quantitative in vivo imaging of entire embryos with Digital Scanned Laser Light Sheet Fluorescence Microscopy", Current Opinion in Neurobiology, 2009, vol. 18, pp. 1-9.

Keller et al., "Reconstruction of Zebrafish Early Embryonic Development by Scanned Light Sheet Microscopy", Science, Nov. 14, 2008, vol. 322, pp. 1065-1069.

Kerr et al., "Imaging in vivo: watching the brain in action", Nature Review, Neuroscience, Mar. 2008, vol. 9, pp. 195-205.

Mavrakis et al., "Lighting up developmental mechanisms: how fluorescence imaging heralded a new era", Development, 2010, vol. 137, pp. 373-387.

McMahon et al., "Dynamic Analyses of *Drosophila* Gastrulation Provide Insights into Collective Migration", Science, Dec. 5, 2008, vol. 322, pp. 1546-1550.

Mertz, "Nonlinear microscopy: new techniques and applications", Current Opinion in Neurobiology, 2004, vol. 14, pp. 610-616.

Olivier et al., "Cell Lineage Reconstruction of Early Zebrafish Embryos Using Label-Free Nonlinear Microscopy", Science, Aug. 20, 2010, vol. 329, pp. 967-971.

Olivier et al., "Two-photon microscopy with simultaneous standard and extended depth of file using a tunable acoustic gradient-index lens", Optics Letters, Jun. 1, 2009, vol. 34, No. 11, pp. 1684-1686.

Palero et al., "A simple scanless two-photon fluorescence microscope using selective plane illumination", Optics Express, Apr. 12, 2010, vol. 18, No. 8, pp. 8491-8498.

Pantazis, et al., "Second harmonic generating (SHG) nanoprobes for in vivo imaging", PNAS, Aug. 17, 2010, vol. 107, No. 33, pp. 14535-14540.

Preibisch et al., "Software for bead-based registration of selective plan illumination microscopy data", Nature Methods, Jun. 2010, vol. 7, No. 6, 20 pgs.

Provenzano et al., "Shining new light on 3D cell motility and the metastatic process", Trends in Cell Biology, 2009, vol. 19, No. 11, pp. 638-648.

Pu et al., "Nonlinear Optical Properties of Core-Shell Nanocavities for Enhanced Second-Harmonic Generation", Physical Review Letters, May 21, 2010, vol. 104, pp. 2074021-2074024.

Schonle et al., "Heating by absorption in the focus of an objective lens", Optics Letters, Mar. 1, 1998, vol. 23, No. 4, pp. 325-327.

Supatto et al., "Quantitative imaging of collective cell migration during *Drosophila* gastrulation: multiphoton microscopy and computational analysis", Nature Protocols, 2009, vol. 4, No. 10, pp. 1397-1412.

Vermot et al., "Fast fluorescence microscopy for imaging the dynamics of embryonic development", HFSP Journal, Jun. 2008, vol. 2, No. 3, pp. 143-155.

Verveer et al., "High-resolution three-dimensional imaging of large specimens with light sheet-based microscopy", Nature Methods, Apr. 2007, vol. 4, No. 4, pp. 311-313.

Voie et al., "Orthogonal-plan fluorescence optical sectioning: three-dimensional imaging of macroscopic biological specimens", Journal of Microscopy, Jun. 1993, vol. 170, Pt. 3, pp. 229-236.

Williams et al., "Interpreting Second-harmonic Generation Images of Collagen I Fibrils", Biophysical Journal, Feb. 2005, vol. 88, pp. 1377-1386.

Zipfel et al., "Nonlinear magic: multiphoton microscopy in the biosciences", Nature Biotechnology, Nov. 2003, vol. 21, No. 11, pp. 1369-1377.

* cited by examiner

LISH

LSM

MULTIPLE-PHOTON EXCITATION LIGHT SHEET ILLUMINATION MICROSCOPE

CROSS-REFERENCE TO RELATED APPLICATIONS

The current application claims priority to U.S. Provisional Application Nos. 61/256,010, and 61/256,005 both cases filed Oct. 29, 2009, the disclosure of which is incorporated herein by reference.

STATEMENT OF FEDERAL FUNDING

The federal government has rights to current invention pursuant to a funding provided in accordance with grant numbers EY018241 and HG004071, issued by the National Institutes of Health, and grant number DBI0852883, issued by the National Science Foundation.

FIELD OF THE INVENTION

The present invention relates generally to light sheet illumination microscopes and microscopy, and more specifically to a light sheet illumination microscope and microscopy technique that uses multi-photon excitation.

BACKGROUND OF THE INVENTION

Advanced optical microscopy techniques offer unique opportunities to investigate biological processes in vivo. The ability to image tissues or organisms in three dimensions (3D) and/or over time (4D imaging) permits a wide range of applications in neuroscience, immunology, cancer research, and developmental biology. (See, e.g., Mertz, *Curr. Opin. Neurobiol.* 14, 610-616, (2004); Kerr, J. N. D. & Denk, W., *Nature Reviews Neuroscience* 9, 195-205, (2008); Friedl, P., *Current Opinion in Immunology* 16, 389-393, (2004); Bousso, P., *Current Opinion in Immunology* 16, 400-405, (2004); Provenzano, P. P., et al., *Trends in Cell Biology* 19, 638-648, (2009); Keller, P. J., et al., *Science* 322, 1065-1069 (2008); McMahon, A., et al., *Science* 322, 1546-1550 (2008); and Mavrakis, M., et al., *Development* 137, 373-387, (2010), the disclosures of each of which are incorporated herein by reference.) Fundamental light-matter interactions, such as light scattering, absorption, and photo-induced biological toxicity, set the limits on the performance parameters of various imaging technologies in terms of spatial resolution, acquisition speed, and depth penetration (how deep into a sample useful information can be collected). Often, maximizing performance in any one of these parameters necessarily means degrading performance in the others. (See, e.g., Ji, N., et al., *Curr. Opin. Neurobiol.* 18, 605-616, (2008) and Vermot, J., et al., *HFSP Journal* 2, 143-155 (2008), the disclosures of each of which are incorporated herein by reference.)

Such tradeoffs in performance are seen in comparing two current well-known 4D fluorescence imaging techniques of two-photon laser scanning microscopy (2p-LSM) and one-photon light sheet (1p-LISH) microscopy: 2p-LSM excels in achieving high depth penetration in scattering tissues, while 1p-LISH allows higher acquisition speed and lower phototoxicity. In 2p-LSM, the images are generated by raster scanning the sample with tightly-focused point of near-infrared (NIR) light, inducing 2p-excited fluorescence signal only at the focus spot and thus generating 3D resolution. (See, e.g. Denk, W., et al., *Science* 248, 73-76 (1990) and Zipfel, W. R., et al., *Nat. Biotechnol.* 21, 1369-1377 (2003), the disclosures of each of which are incorporated herein by reference.) Signal and spatial resolution are maintained significantly deeper into scattering samples compared with modalities that use 1-photon excitation (such as confocal laser scanning microscopy (CLSM)), due to (i) the low scattering of NIR light, and (ii) the efficient non-imaging detection where both ballistic and scattered fluorescence photons contribute to the signal (as the 3D resolution is achieved through confinement of the excitation alone). The acquisition speed of 2p-LSM is, however, limited since the image is collected one voxel at a time.

1p-LISH microscopy is a century-old technology that has seen much development and refinement in recent years, under names ranging from Orthogonal. Plane Fluorescence Optical Sectioning (OPFOS), Thin Laser light Sheet Microscopy (TLSM), Selective Plane Illumination Microscopy (SPIM) (FIG. 1A, high-speed imaging of live zebrafish heart), Objective Coupled Planar Illumination (OCPI) (FIG. 1B, high-speed calcium imaging of neurons), ultramicroscopy (FIG. 1C, blood vessel system of mouse embryo), and Digital. Scanned Laser Light Sheet Fluorescence Microscopy (DSLM) (FIG. 1D, in toto imaging of developing zebrafish embryo), among others. (See, e.g., Siedentopf, H. & Zsigmondy, R., *Ann. Phys.-Berlin* 10, 1-39 (1902); Voie, A. H., et al., *J. Microsc.-Oxf.* 170, 229-236 (1993); Fuchs, E., et al., *Opt. Express* 10, 145-154 (2002); Huisken, J., et al., *Science* 305, 1007-1009 (2004); Holekamp, T. F., et al., *Neuron* 57, 661-672 (2008); Dodt, H. U. et al., *Nat. Methods* 4, 331-336 (2007); Huisken, J. & Stainier, D. Y. R., *Development* 136, 1963-1975 (2009); and Keller, P. J. & Stelzer, E. H. K., *Curr. Opin. Neurobiol.* 18, 624-632 (2008), the disclosures of each of which are incorporated herein by reference.)

In 1p-LISH, (FIG. 1E) a planar sheet of light is used to illuminate the sample, generating fluorescence signal over a thin optical section of the sample, which is then imaged from the direction orthogonal to the light sheet, with a wide-field imaging camera. Axial sectioning results from the thinness of the light sheet, while lateral resolution is determined by the detection optics. The orthogonal geometry between the illumination and detection pathways of 1p-LISH, compared to the collinear geometry of conventional microscopes, not only enables higher imaging speed due to the parallel image collection (millions of voxels can be imaged simultaneously), but also reduces phototoxicity since only a single focal plane of the sample is illuminated at a time. The depth penetration of 1p-LISH into scattering biological tissue, however, is limited (only slightly better than CLSM), due to (i) the imaging requirement of the wide-field detection that requires ballistic fluorescence photons only and scattered photons would degrade the image quality, and (ii) the light sheet is spatially degraded beyond its original thinness due to scattering, as it is focused deep inside an optically heterogeneous sample.

Accordingly, it would be advantageous to develop an optical microscopy technique that strikes a new balance between the imaging performance of 2p-LSM and 1p-LISH capable of providing new imaging capabilities heretofore unobtainable with conventional microscopy techniques.

SUMMARY OF THE INVENTION

The present invention is directed to a multiple-photon excitation light sheet microscope, where the optical signal contrast is generated by an excitation process that involves multiple (more than one) photons. In such an embodiment, if S equals such optical signal, and I the excitation light intensity, then S is proportional to $I^n$, where n is equal to or greater than 2, for a process that involves n photons. For example, for a two-photon process, n=2, for a three-photon process, n=3.

In one embodiment, the microscope includes an excitation laser source that provides sufficiently high light intensity to induce significant levels of multiple-photon excitation.

In another embodiment, the excitation source is a pulsed laser producing radiation in the near-infrared wavelength range (approximately 0.7-1.4 microns), having a pulse duration in the range of nanosecond, picosecond, or femotosecond.

In yet another embodiment, the detected signal contrast can be two-photon-excited fluorescence, second harmonic generation, third harmonic generation, sum frequency generation, and stimulated Raman scattering.

In still another embodiment, the microscope includes excitation focusing optics for producing a substantially two-dimensional sample excitation region which extends in the direction of an excitation axis of the excitation beam path and transversely thereto and intersects with at least a portion of the sample holder.

In yet another embodiment, the microscope includes an imaging detector disposed such that the detection direction is substantially orthogonal to the sample excitation region. In such an embodiment, the imaging detector may be a charged-coupled device camera, which is a detector that registers the optical signal simultaneously with an array (one or two-dimensioned) of light sensitive elements, capturing an image of the sample.

In still yet another embodiment, the excitation focusing optics of the microscope includes a spherical lens through which the excitation beam is focused, and the excitation beam is laterally scanned along a desired axis of the excitation beam to form an effectively uniform excitation intensity across said excitation region.

In still yet another embodiment, the excitation focusing optics of the microscope includes a cylindrical lens, and the sample excitation region is created by statically focusing the excitation beam through said cylindrical lens.

In still yet another embodiment, the excitation source is capable of creating two coaxial and oppositely aligned excitation beams, such that said sample excitation region is formed from the overlap of the two excitation beams.

In still yet another embodiment, the numerical aperture of the excitation focusing optics is adjustable. In one such embodiment, the adjustable numerical aperture includes a beam expander with an adjustable expanding ratio.

In still yet another embodiment, a so-called focal-volume-engineering process is applied to the excitation beam to optimize the focal region for light sheet imaging. Such focal volume engineering can be implemented by optical devices such as adjustable slit apertures, beam expanders, spatial light modulators, and so on, operated separately or in tandem.

In still yet another embodiment, as an example of the focal volume engineering that can be applied, the numerical aperture of the excitation focusing optics is anisotropic along at least two axes of said excitation beam. This could be obtained by having two sequential adjustable slit apertures oriented so that the slits are orthogonal to each other, or by a spatial light modulator.

In still yet another embodiment, the excitation beam could be transformed, via an axiconic lens or a spatial light modulator, to have the so-called Bessel beam profile (instead of the standard Gaussian beam profile). A focused Bessel beam could provide a larger field of view for LISH imaging, for the same thickness at the center of the light sheet.

In still yet another embodiment, the microscope includes a sample holder that is moveable relative to the sample excitation region along or about at least one axis.

In still yet another embodiment, the microscope includes a sample excitation region that is moveable relative to the sample holder along or about at least one axis.

In still yet another embodiment, the excitation region is one of either substantially planar-shaped or linearly-shaped.

The invention is also directed to a method of imaging an object using a multiphoton light sheet microscope.

BRIEF DESCRIPTION OF THE DRAWINGS

These and other features and advantages of the present invention will be better understood by reference to the following detailed description when considered in conjunction with the accompanying drawings and data, wherein.

DETAILED DESCRIPTION OF THE INVENTION

The current invention is directed to a novel multi-photon light sheet (MP-LISH) microscope and microscopy technique. The technique and device use a multi-photon excitation light to generate signal contrast in the light sheet, thus exploiting both the nonlinear excitation to achieve high depth penetration and the orthogonal geometry of light sheet to achieve high acquisition speed and low phototoxicity.

Conventional LISH Microscopy

Figure 1A:
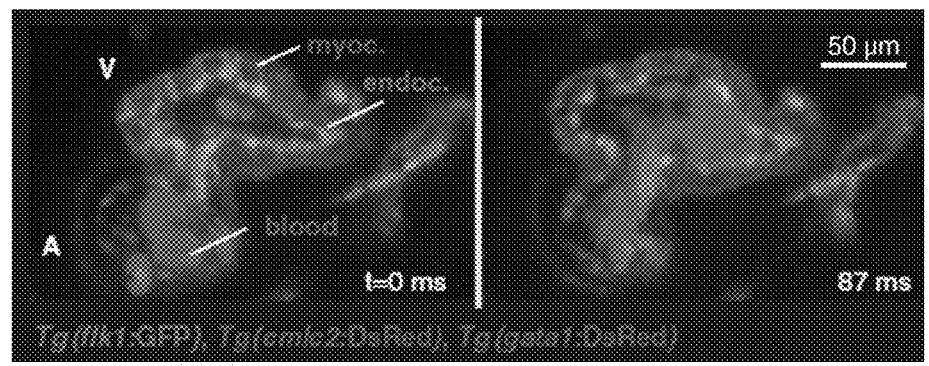
FIGS. 1A to 1D provide images and data from experiments taken using: (A) SPIM; (B) ultramicroscopy; (C) OCPI; and (D) DLSM.
Figure 1B:
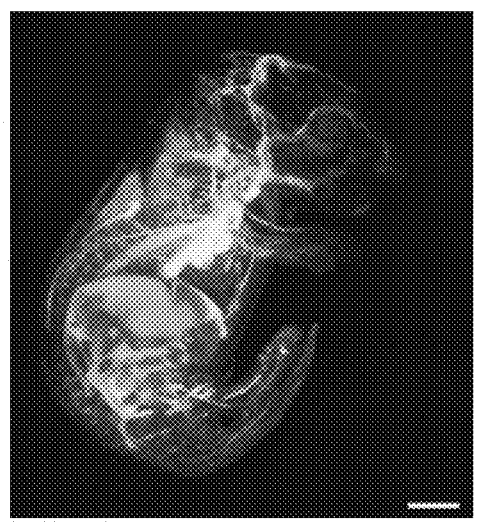
Figure 1C:
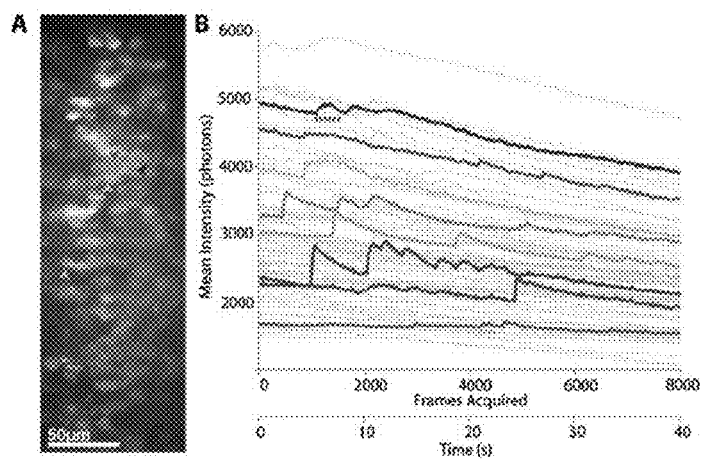
Figure 1D:
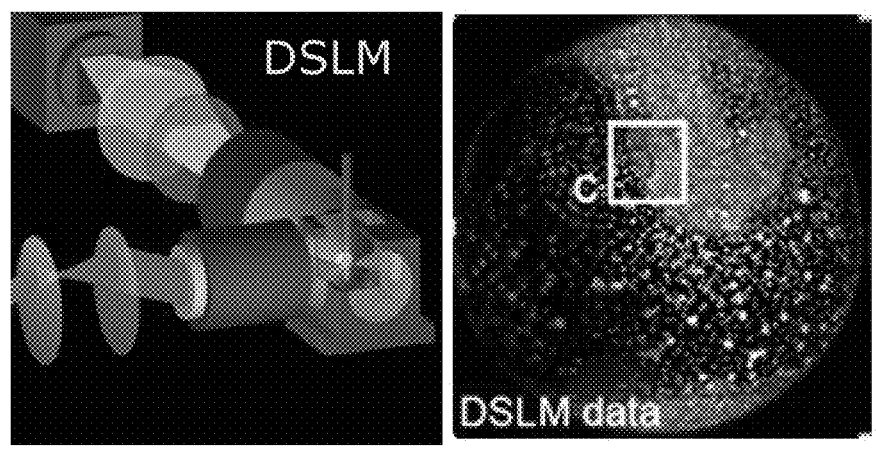
Figure 1E:
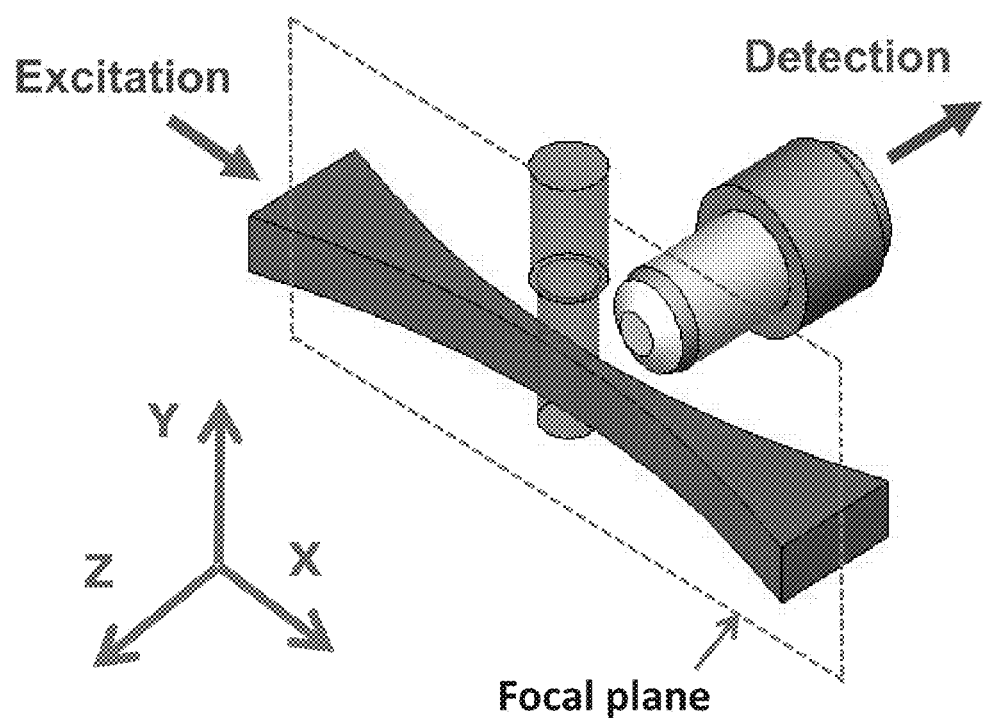
FIG. 1E provides a schematic of a conventional 1p-LISH microscope.

A schematic of a conventional 1p-LISH microscope is provided in FIG. 1E. As shown, LISH is a microscopy technique where the illumination is done from the side of the sample, creating a diffraction-limited planar sheet of light going across the sample. (See, J. Huisken and D. Y. R. Stainier, *Development* 136, 1963-1975 (2009), the disclosure of which is incorporated herein by reference.) Detection of the emitted light is done at 90 degrees from the illumination direction, orthogonal to the light sheet. Z-sectioning is achieved since only one diffraction-limited plane is illuminated at a time. The sample may be scanned through the plane (or inversely the plane could be scanned through the sample) to allow coverage of the whole sample volume. Axial resolution of a LISH microscope is determined by the thinnest of the sheet and the detection optics. Lateral resolution of a LISH microscope is determined by the detection optics alone. The imaging field of view of a LISH microscope is determined by the so-called confocal parameter of the illumination, defined as the distance about the focus spot where the sheet thickness remains less than the squareroot of 2 times its smallest value.

LISH microscopy differs from laser or raster-point-scanning (LPS or RPS) microscopy in the geometry of the illumination and detection optical pathways. RPS microscopy, which is a widely used imaging technology, uses a collinear (parallel or anti-parallel) geometry between the illumination and detection pathways. (See, e.g., Pawley, *Handbook of Confocal Microscopy*, 3$^{rd}$ Edition, New York: Springer (2006), the disclosure of which is incorporated herein by reference.) This results in some inherent advantages for LISH microscopy. In particular, because of the orthogonal geometry between the illumination and detection directions, the lateral extent of the illumination focus (together with the detection optics) determines the axial resolution of the final image. Compare this with conventional LSM, where the final axial resolution is determined by the axial extent of the illumination focus. Since for a given focusing NA, the focus spot is always smaller laterally than axially, 2p-LISH needs to employ a substantially smaller focusing NA than conventional 2p-LSM to reach the same axial resolution (by a factor of approximately 10), which carries important implications, as will be discussed in detail later. In addition, particularly for imaging 3D biological samples, illumination in LISH is limited only to the plane that is being imaged, hence reducing photobleaching and phototoxicity; detection is done in parallel for the whole plane, usually with a CCD camera, hence time acquisition is fast, usually about 10-20 times faster than the LSM technique.

Because of these inherent advantages, conventional 1p-LISH has been the subject of intensive study, and the literature discloses many recent implementations of the conventional LISH technique. (See Huisken and Stainier, referenced above.) Some of these techniques include Orthogonal Plane Fluorescence Optical. Sectioning (OPFOS), Selective Plane Illumination Microscopy (SPIM), Ultramicroscopy, Digital Scanned Laser Light Sheet Fluorescence Microscopy (DSLM), etc. Although these different implementations have different specialized features, they have one common critical feature: the illumination is done with a sheet of light orthogonal to the detection direction. In the DSLM technique, the light sheet is synthesized by scanning, via a movable device such as a galvanometer mirror, a low-NA focused beam of light. Seen from the side through the detection objective, the focused beam of light appears as a line of light. At any time instant the sample is illuminated by only a line of illumination, which when summed over the scanned space and over time, yields an illuminated light sheet.

Figure 2A:
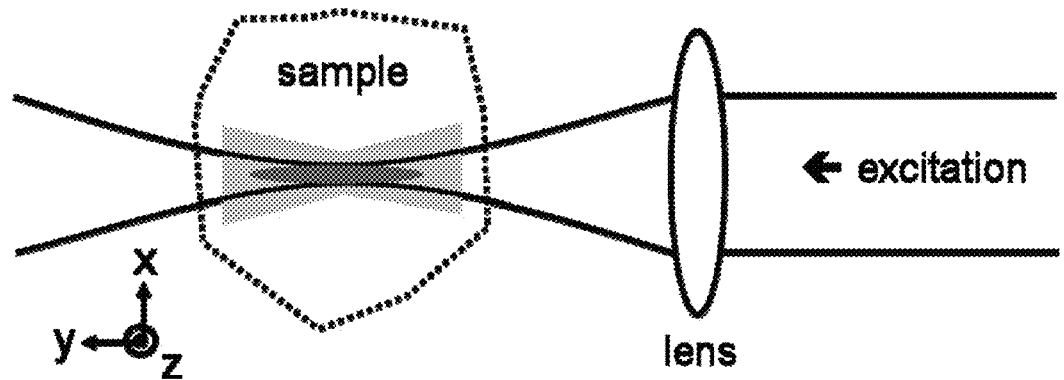
FIG. 2A provides an optical schematic of a line illumination scheme, contrasting the spatial extent of the emitted signals from one-photon and multiphoton excitation.
Figure 2B:
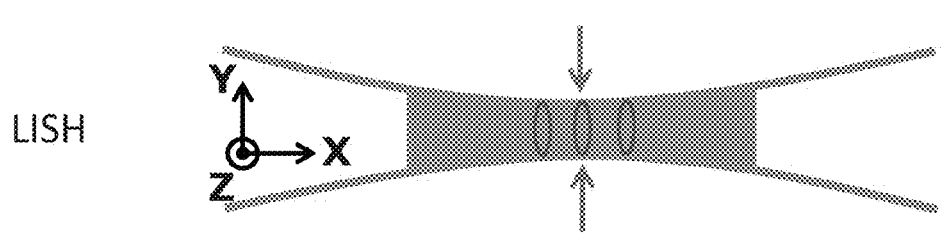
FIG. 2B provides schematics of the excitation region of both LSM and LISH microscopes.
Figure 2B:
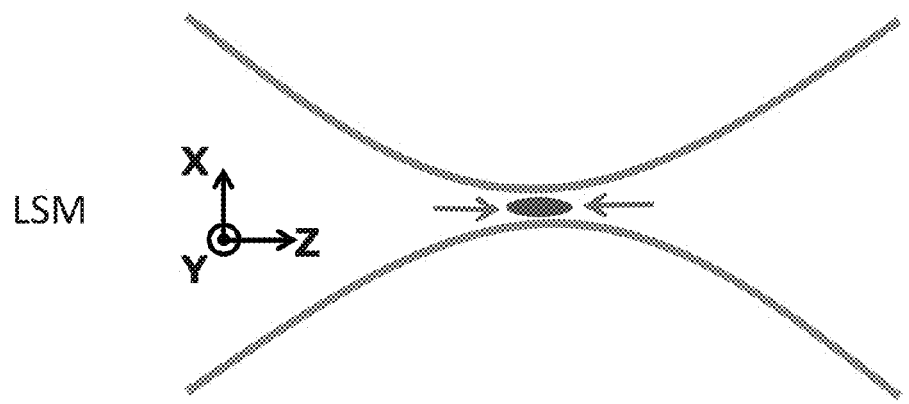

As the light sheet travels into the samples, scattering (and/or refraction) causes the light to diffuse out, degrading the diffraction-limited quality of the illumination light. As the light sheet degrades, its spatial extent increases and its sharpness decrease. Since the emitted signal is proportional to the instantaneous light intensity l at the sample, when l is spatially spread out, so is the signal. Hence, spatial resolution and signal contrast are degraded for thick samples. This phenomenon is illustrated in FIG. 2, which provides an optical schematic of line illumination scheme, showing the spatial extent of the emitted signals a LISH excitation. The lens represents the illumination objective, component. The figure shows the view as seen by the detector, looking along the −z direction towards the sample. Solid focusing lines depict the light propagation if there were no scattering/refraction in the sample. The light gray area depicts the spatial extent of the emitted signals from one-photon excitation, as the light sheet is degraded and diffused out due to scattering/refraction. This establishes for LISH microscopy an excitation depth penetration, i.e. the depth into a sample beyond which the light sheet has degraded so much that no useful information can be collected. Also, since the samples, particularly biological ones, are usually nonhomogeneous, the effects of scattering/refraction cause the light sheet intensity to be nonhomogeneous, and thus introducing artifacts into the resulting detected image.

Inventive MP-LISH Microscopy

The current invention describes a LISH microscope that uses multi-photon excitation to generate signal contrast, thus exploiting both the nonlinear excitation to achieve high depth penetration and the orthogonal geometry of light sheet to achieve high acquisition speed and low phototoxicity.

The literature discloses a technique that reduces the detrimental effect of scattering/refraction to imaging: multiphoton (MP) excitation. In standard single photon (SP) excitation, one photon of the illumination light interacts with the sample and gives rise to an emitted photon (usually in the form of fluorescence). In MP excitation, the excitation step involves n number of photons, where n is equal to or greater than 2. The multiple number of photons interact with the sample essentially simultaneously, and then give rise to emitted radiation, which could be in the form of fluorescence, second harmonic generation, third harmonic generation, etc. (See, J. Pawley, *Handbook of Confocal Microscopy*, 3$^{rd}$ Edition, New York: Springer (2006), the disclosure of which is incorporated herein by reference.) For MP excitation, the excitation probability, and hence the emitted signal, is proportional to $I^n$, where I is the instantaneous intensity of the laser light at the sample. This can be contrasted with the SP case, discussed above, where the signal is proportional to l.

Because of the $I^n$ dependence of the emitted signal in MP excitation, the signal is confined to a small region of space where $I^n$ is above a certain threshold. Thus, as the laser light undergoes scattering/refraction and diffuse out in space in the sample, the signal intensity would decrease, but the signal would still only comes from a small volume, hence preserving the resolution. This phenomenon is shown schematically in FIG. 2A, where the spatial extent of the emitted signal from multiphoton excitation is restricted to the dark gray region, even though the light beam is degraded and spread out beyond it, due to the spatial confining effect of multiphoton excitation processes.

In addition, MP excitation typical uses illumination light in the near infrared range, with wavelengths longer than visible light that is normally used for SP excitation, thus scattering effects are reduced since the scattering cross-sections of biological molecules are inversely proportional to the wavelength to the m power, where m is a number greater than zero.

Finally, the longer wavelengths of MP excitation are also generally less phototoxic for biological samples, since there is less endogenous absorption from biomolecules at these wavelengths.

Because of these advantages, MP excitation has been applied to LSM microscopy, and has been confirmed to have the above-mentioned advantages over SP-LSM microscopy. (See, J. Pawley, (2006), cited above.) However, despite these inherent advantages, no attempt has ever been made to apply MP excitation to LISH, and all implementations of LISH up to date have used excitation light in the visible range, ~400-700 nm, and relying on SP processes to create the detected emitted light. (Examples of these one-photon processes include 1-photon absorption and fluorescence and Raleigh scattering.)

The reason for this lack of interest is that developing a light sheet microscope based on multi-photon excitation has, in the past, raised concerns about whether sufficient fluorescence signal can be generated without reaching phototoxic levels of laser power when using low-NA-focused excitation light. However, it has been surprisingly discovered that with a spherically-focused beam, the average excitation probability within the focal volume for 2p excitation is proportional to $NA^4$, and the total focal volume is proportional to $NA^{-4}$, hence the total excitation (given by the excitation probability times the focal volume) is independent of the focusing NA for a homogeneous distribution of fluorophores. (See, Zipfel, W. R., et al., *Nat. Biotechnol* 21, 1369-1377 (2003), the disclosure of which is incorporated herein by reference.)

Figure 3:
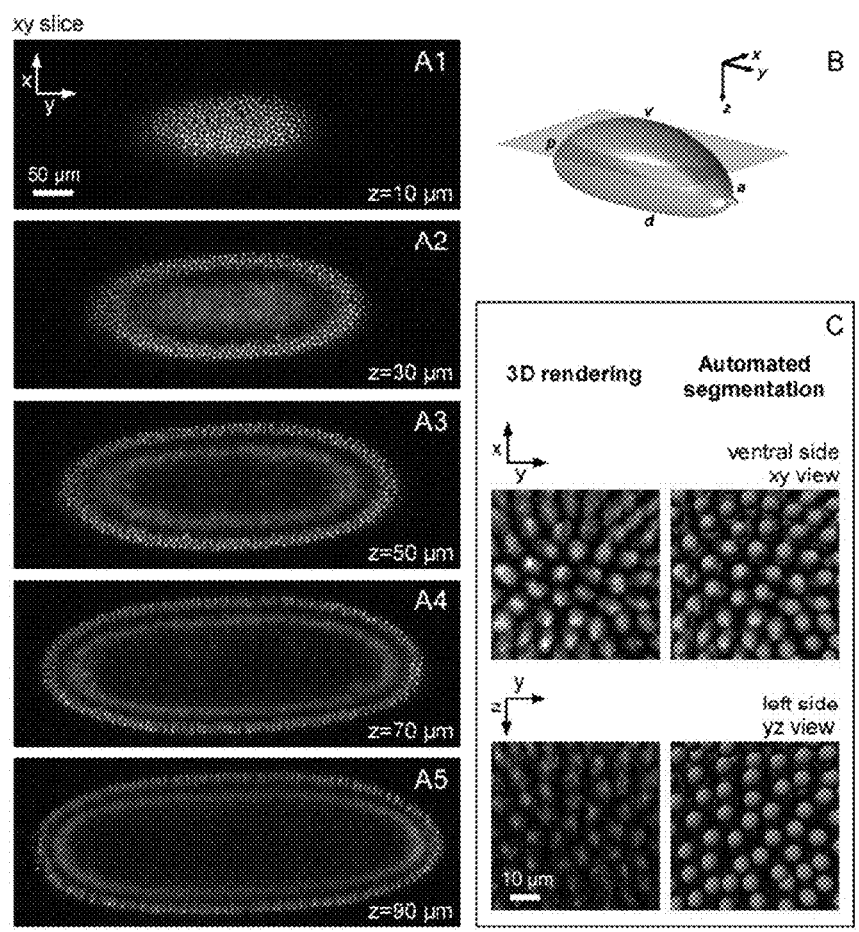
FIGS. 3A to 3C provides images and data of fly data before gastrulation at stage 5 slices at different planes: (A1-5) of an embryo imaged using 2p-LISH with the ventral side facing the detection objective, (B) and the light sheet along the xy-plane entering the embryos from lateral sides, and (C) with automated segmentation of nuclei using standard software both on the ventral nuclei (C, up) and the lateral side (C, down)

Thus, it has now been determined that 2p-LISH and conventional 2p-LSM should have the same average signal rate in imaging an extended 3D sample, under the same average laser excitation power, spatial sampling density (voxel size), and detection efficiency. This counter-intuitive result could be understood in another way by noting that even though for 2p-LSM the instantaneous signal rate at each voxel is higher due to the tighter focusing, these voxels are illuminated one at a time, while in 2p-LISH an entire row of voxels is being illuminated and imaged simultaneously. (This is illustrated schematically in FIG. 2B.) Hence longer voxel exposure time could be used in 2p-LISH to compensate for the lower instantaneous signal rate, making the final signal rate equal for the two modalities. As will be described in greater detail below, this result was experimentally verified by imaging a live *Drosophila* embryo with 2p-LISH, using imaging parameters that are typically used for 2p-LSM (acquisition time of 1 sec for frame of 400×900 pixels, and total average power of 30 mW at the sample). The acquired images (FIG. 3A) have approximately the same signal quality as that obtained through 2p-LSM with similar imaging parameters and samples: for instance, the signal-to-noise ratio (SNR) is high enough to permit automated nuclear segmentation with standard image processing software (FIG. 3B). (See, Supatto, W., et al., *Nature Protocols* 4, 1397-1412 (2009), the disclosure of which is incorporated herein by reference.)

Another reason that further makes developing a light sheet microscope based on multi-photon excitation a non-obvious choice is that, even if it is realized that the signal rate is the same in 2p-LISH as in 2p-LSM, already a non-obvious realization as described in the previous paragraph, it can still be argued then that precisely because of the same signal rate between the two imaging modalites, 2p-LISH would have minimal benefit over the already established and well-commercialized technique of 2p-LSM. That is, the same inherent signal rate means that with the same excitaiton laser power, 2p-LISH is expected to achieve the same, not higher, image acquisition speed as 2p-LSM. Thus, while 2p-LISH is expected to have an advantage over 1p-LISH in depth penetration (see discussion above), it seemingly is not expected to have any advantage over the existing technique of 2p-LSM (which already employs the same two-photon excitation mechanism and hence would have about the same depth penetration), and hence, not worthy for development.

The advantage of 2p-LISH over 2p-LSM comes from its lower phototoxicity quality, which comes from the usage of lower focusing NA resulting in lower peak excitation intensity. Because of the lower phototoxicity of 2p-LISH compared to 2p-LSM (the reasons for which will be demonstrated and discussed further below), more laser excitation can be used in 2p-LISH than in 2p-LSM in imaging a live biological sample before the onset of phototoxicity, thus yielding a higher signal rate and hence higher acquisition speed. Thus, one of the key advances in developing 2p-LISH lies critically in realizing the low phototoxicity quality of 2p-LISH compared to the conventional technique of 2p-LSM.

The same signal rate of 2p-LISH and 2p-LSM is a result specific to the 2-photon excitation process. If the excitation process involves more than 2 photons, then the signal rate of the LISH modality will have less signal rate than the LSM counterpart. For example, 3-photon-excited fluorecence LISH microscopy will have lower signal rate than 3-photon-excited fluorescence LSM. Then the advantage of 3p-LISH over 3p-LSM would be less than that of 2p-LISH over 2p-LSM. However, the low phototoxicity quality, due to the low focusing NA, of 2p-LISH is expected to be still valid for MP-LISH involving more than 2 photons. Thus, MP-LISH is still expected to be able to tolerate higher laser excitation power before the onset of phototoxicity as compared to MP-LSM, thus possibly the higher laser power could make up for the decreased signal rate, and thus still renders MP-LISH more advantageous over MP-LSM.

Figure 4:
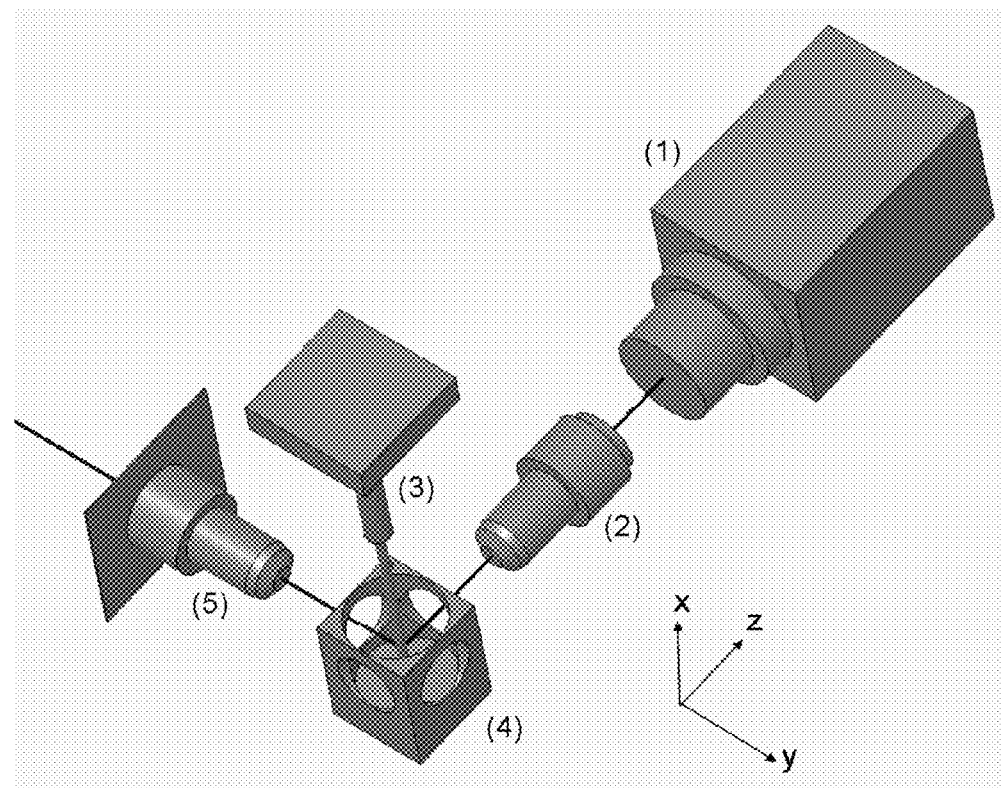
FIG. 4 provides a schematic of a MP-LISH microscope in accordance with the current invention.

Turning to the MP-LISH microscope itself, the apparatus of the current invention is shown schematically in FIG. 4. As shown, the basic MP-LISH setup includes an illumination objective (5) positioned along a first axis of a sample chamber (4). The sample chamber is attached to a sample holder and controller (3), preferably allowing control in x,y,z, and theta (rotational). A detection objective (2) and imaging device, such as, for example, a camera (1) are positioned in line of sight to the sample chamber along a second axis that is orthogonal to the first illumination axis. Black solid lines depict the optical axis of the illumination and detection beams, going through (5) and (2), respectively. Not shown are the mechanical supports of the system. (For a detailed description of a LISH microscope see, US Pat. Pub. No. 2009/0225413, the disclosure of which is incorporated herein by reference.)

Comparing FIGS. 1E and 4 it becomes clear that the apparatus for MP-LISH (FIG. 4) is facially similar to that used for 1p-excited fluorescence DSLM (FIG. 1). (See, Keller, P. J., et al., Science 322, 1065-1069 (2008), the disclosure of which is incorporated herein by reference.) However, there are several critical changes: provisions must be made to send in the pulsed laser light along the illumination path, this includes ensuring that all of the optical components are compatible with the pulsed laser light (e.g. mirrors should reflect enough of that particular wavelength of the pulsed laser light so that illumination intensity is high enough to induce a multi-photon process at the sample, or that the optical components are not damaged by the high energy/intensity of the pulsed laser beam.) In turn, the detection pathway must be modified to include the addition of extra short-pass optical filter(s) to screen out the illumination radiation, which has longer wavelengths than the emitted signal radiation. Finally, because in MP-LISH microscopy, the signal depends very sensitively on the illumination NA, attention must be paid to achieve the optimal illumination NA, so that the highest signal level is achieved with an acceptable field of view. In practice, it turns out that for the same samples, one would need to use higher NA for MP than for SP excitation, and relying on additional methods to increase the field of view, as will be discussed in greater detail below).

As will be described in greater detail in the exemplary embodiments to follow, the use of MP excitation in LISH microscopy as described herein improves the performance of the LISH microscope, particularly to mitigate the detrimental effects of scattering/refraction in samples, biological or non-biological The MP excitation is used to produce the emitted radiation signals, which could be, but are not restricted to, fluorescence, second harmonic generation, third harmonic generation, sum frequency generation, and stimulated Raman scattering.

In carrying out the MP excitation, any suitable source of excitation energy may be utilized, however, in a preferred embodiment pulsed lasers are used in order to achieve the high instantaneous intensities required to produce significant levels of emitted signals (which are proportional to $I^n$ for MP excitation processes). The puked lasers can be of any suitable type, such as, for example, nanosecond, picosecond, or femtosecond-duration pukes. The shorter the puke, the lower the total laser energy is needed to achieve the same level of instantaneous intensity. In light of this, for biological samples, in order to minimize thermal damage, femtosecond pukes (with duration of hundreds of femtosecond or shorter) are preferred. In turn, picosecond and nanosecond pulses might be more appropriate for non-biological samples, where thermal damage is less of a concern.

Scanned Light Sheet

In carrying out the MP excitation, the scanned sheet (via scanning of a line illumination) (as described in the DLSM technique) is preferred over the static sheet illumination. (See, J. Huisken & D. Y. R. Stainier, Development 136, 1963-1975 (2009), the disclosure of which is incorporated herein by reference.) The smaller spatial extent of the line, as compared to the sheet, helps to achieve high instantaneous intensity while minimizing total light energy irradiated onto the sample.

Figure 5:
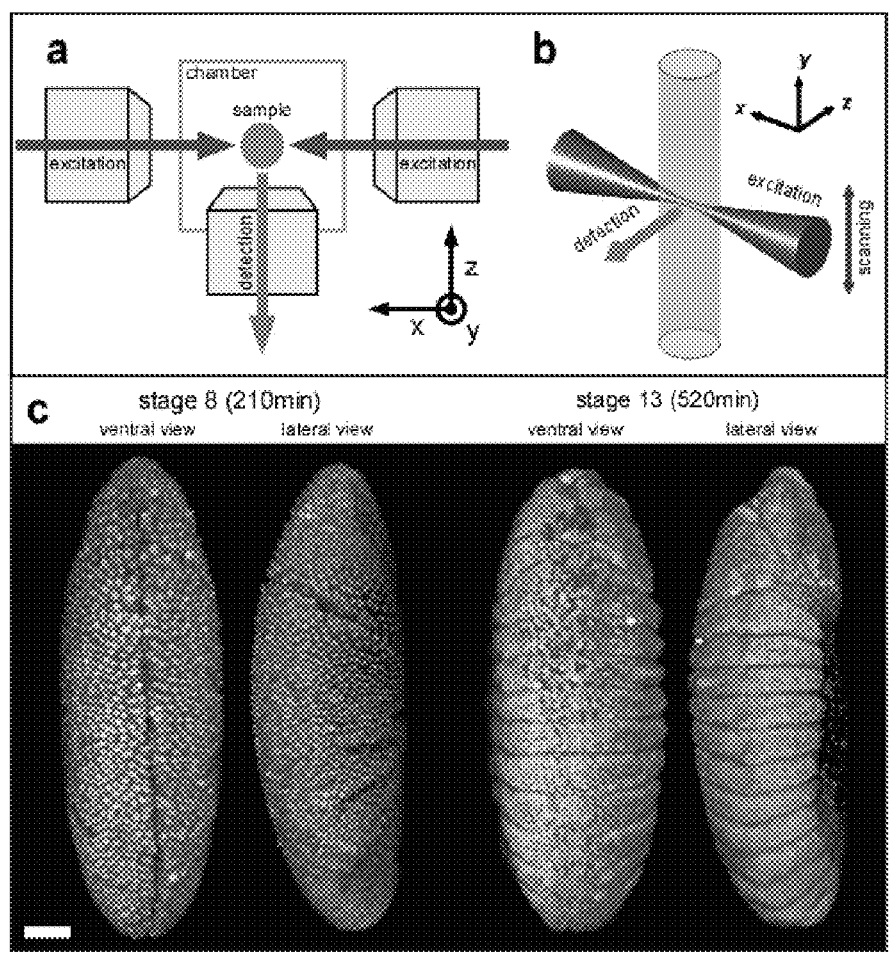
FIGS. 5A to 5C provide schematics of and data from a MP-LISH microscope using a scanned light sheet where: (A) shows a top view schematic of setup around the sample area, where (B) the illumination light sheet (xy-plane) is generated by fast laser scanning in the y-direction, and (C) shows 3D renderings of a live *Drosophila* embryo at stage 8 (left) and stage 13 (right) with nuclear labeling (H2A-GFP) imaged with 2p-LISH, showing the ventral and lateral views, where the scale bar=50 µm.

Although a static light sheet, as shown schematically in FIG. 1E may be used with the MP-LISH apparatus of the current invention, in the preferred embodiment, shown schematically in FIG. 5A, the illumination light sheet is created by the fast lateral scanning along the y direction of the spherically-focused laser light (red in FIG. 5A-B), generating a scanned sheet along the xy-plane, perpendicularly to the z detection axis (green in FIG. 5A-B). (See, Keller, P. J., et al., (2008), cited above.) (It should be noted that although the illumination is bidirectional in this figure, that a scanned light sheet may be generated in with a unidirectional excitation source. A more detailed examination of the advantages of bidirectional excitation sources will be provided below.)

A scanned light sheet can be generated by fast scanning of the beam, with a period of 1 ms to cover the full FOV. This kHz-speed is fast enough to produce an effectively uniform illumination intensity across the y-extent of the FOV, for imaging exposure times of tens of ms or more. For shorter exposure times, faster scanning hardware could be employed (e.g. resonant scanners or spinning polygon mirrors can scan in the range of 10-100 kHz). In this embodiment, the lateral extent of the illumination focus spot determines the thickness of the scanned light sheet, while the confocal parameter of the focal region (the distance over which the lateral extent remains less than two times its smallest value) determines the imaging field of view.

As will be described in greater detail below, the scanned sheet feature provides dramatic and unexpected improvements in imaging capabilities for the inventive MP-LISH over the conventional static sheet, which is typically produced by focusing through a cylindrical lens. (See, Huisken, J., et al., Science 305, 1007-1009 (2004) and Palero, J., et al., Opt. Express 18, 8491-8498 (2010), the disclosures of each of which are incorporated herein by reference.) An example of the performance of this 2p-LISH system in live imaging of Drosophila and zebrafish embryos is shown in FIG. 5C. The data illustrates the striking results that could be obtained with this new imaging modality, by showing multi-view 3D renderings of a live Drosophila embryo at two time points in its embryonic development, exhibiting fine spatial resolution achieved even deep inside the embryo, all done at high enough imaging speed and negligible phototoxicity so that fast cellular dynamics could be followed throughout the entire embryonic development. In short a two-fold increase was found in depth penetration compared with 1p-LISH, and more than an order of magnitude increase in imaging speed compared to 2p-LSM, allowing 70 frame-per-second imaging of the beating heart inside a 5.4-day-old zebrafish.

A scanned sheet implementation of LISH microscopy is advantageous over a static sheet by achieving higher excitation power throughput, better spatial uniformity along y-dimension of the FOV, and allowing convenient execution of non-coherent structured illumination to improve signal contrast. (See, Keller, P. J., (2008); and Keller, P. J. et al., Nat. Methods 7, 637-(2010), the disclosures of each of which are incorporated herein by reference.) In addition, it has been recently demonstrated that the scanned light sheet minimizes scattering artifacts compared to the static light sheet illumination used in SPIM. (See, Fahrbach, F. O., et al., cited below.) All of these benefits of scanned sheet versus static sheet exist in both 1p- and 2p-LISH.

For the case of 2p-LISH, the spherically-focused scanned light sheet further yields an additional critical benefit over the cylindrically-focused static light sheet, in producing significantly more nonlinearly-excited fluorescence signal for the same average excitation power. In fact, for the same excitation power, the signal rate from the scanned sheet is higher than from the static sheet by a factor equals to the ratio of field of view in y divided by sheet thickness, which is about 200 in our experimental implementation. This can be seen in the following analysis.

Figure 6:
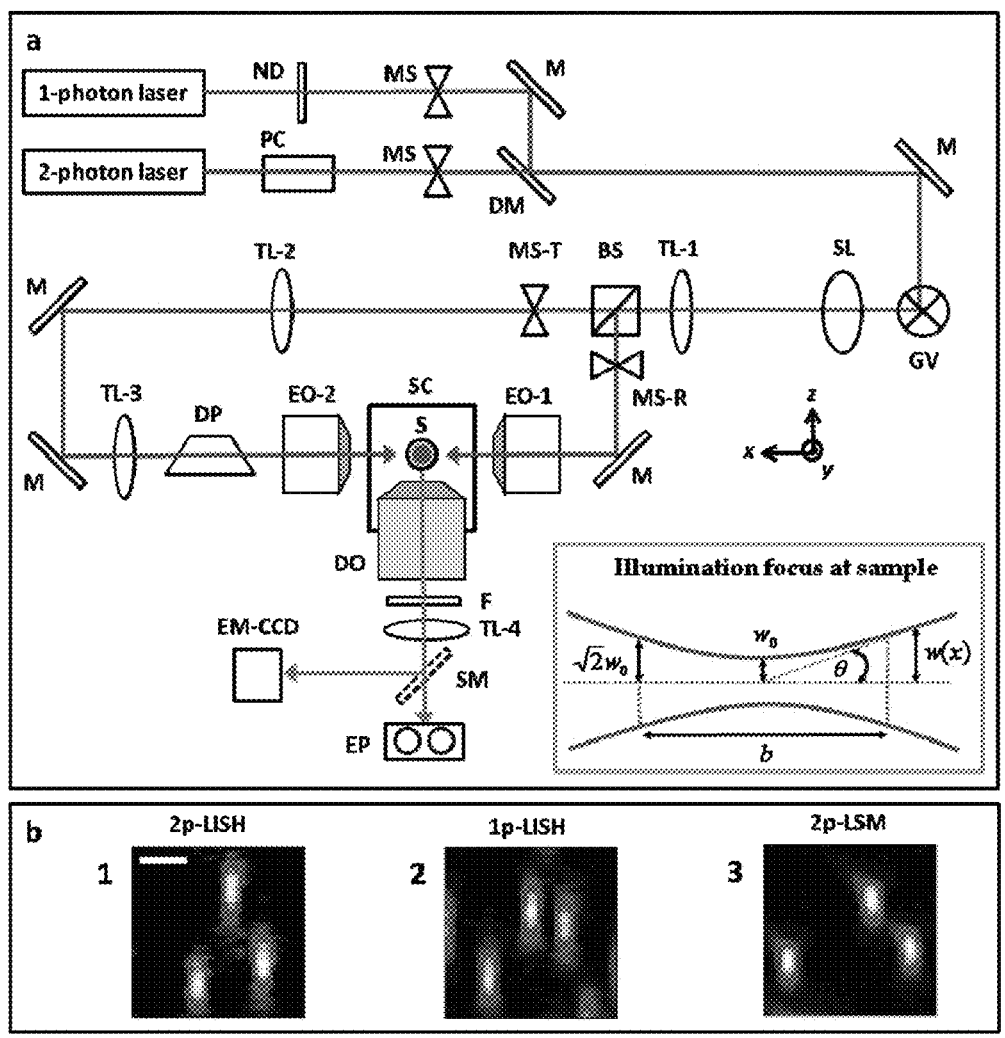
FIGS. 6A & 6B provide: (A) schematic of the main components of the two photon light sheet microscopy setup; and (B) imaging performance parameters of the setup including maximum intensity projections of representative xz-slices of sub-diffraction fluorescent beads imaged by 2p-LISH (B1), 1p-LISH (B2), and 2p-LSM (B3), were the scale bar=3 µm.

Referring to the coordinate system definition in FIG. 6 and its inset described below, a comparison can be made between a scanned light sheet spherically focused to a certain characteristic width $\omega_0$ in both the z- and y-directions, and a static light sheet cylindrically focused to the same width $\omega_0$ in the z direction while being uniform in the y direction over a range of $\omega_0$, with N being a positive real number. $\omega_0$ denotes the extent of the FOV in the y-direction (in the experimental implementation described below, yielding a field of view of about µm with $\omega_0$ µm). The excitation intensity equals the average excitation power divided by the beam cross-sectional area, and thus is given by:

$$I \propto \frac{P}{w_0^2} \quad \text{[scanned sheet]} \qquad \text{[EQ. 1]}$$

and $$I \propto \frac{P}{Nw_0^2} \quad \text{[static sheet]} \qquad \text{[EQ. 2]}$$

where P is the same average excitation power used in both cases. The 2p-excited fluorescence signal rate, which is proportional to the squared of the intensity, averaged over the full extent of $N\omega_0$ along the y-direction, is then:

$$S \propto \frac{1}{N} \frac{P^2}{w_0^4} \quad \text{[scanned sheet]} \qquad \text{[EQ. 3]}$$

and $$S' \propto \frac{1}{N^2} \frac{P^2}{w_0^4} \quad \text{[static sheet]} \qquad \text{[EQ. 4]}$$

The reduction of the signal by the factor of (1/N) for the scanned sheet case in Eq. (3) above reflects the scanning that has to be done for the wide beam to cover the wide FOV along the y-direction, producing an effective spatial duty cycle of (1/N). It can be seen then from EQs. (3) and (4) that the average signal in the scanned sheet case is a factor of N larger than in the static sheet case, using the same excitation power. This comes directly from the quadratic dependence of the 2p-excited fluorescence signal on the excitation intensity. Since experimentally N is in the range of a few hundred, the difference between the two signals is significant. This substantially higher signal rate from the scanned sheet is critical in allowing optimized usage of the light power levels available from commercial laser sources in imaging of biological samples without inducing phototoxicity, as will be discussed further in the discussion section below.

Alternative MP-LISH Embodiments

Bidirectional Illumination:

To increase the field of view of MP-LISH, the illumination may be done from opposite sides of the sample. A schematic of an MP-LISH apparatus including a bidirectional light source is provided in FIGS. 5A-B. As shown, in this embodiment, the illumination beams from the +x and −x directions are adjusted so that their fields of view slightly overlap at the center of the sample, effectively doubling the final field of view. In the literature it has been shown that bidirectional illumination would also improve SP-LISH, but in this case, because of the degraded light sheet, the illumination from opposite sides has to be done sequentially, then the two resulting images have to be merged computationally later to yield the final image (See, Huisken, J. & Stainier, D. Y. R., *Opt. Lett.* 32, 2608-2610 (2007), the disclosure of which is incorporated herein by reference.) In the case of MP-LISH, because the signal is spatially confined due to its I^n dependence, the illumination from opposite could be done concurrently, saving in time acquisition and complexity of data acquisition controls. The resulting image would then have about twice the field of view, with the same resolution and contrast as illuminated from one side at a time.

Adjustable Illumination NA:

The ability to adjust the NA of the illumination may be used to provide greater flexibility for the MP-LISH technique, since the signal depends quite sensitively to the NA, as described above. One way to achieve this is to have the illumination light go through a beam expander with adjustable expanding ratio, which then yields an adjustable illumination beam diameter, which in turns allow for fine-tuning the illumination NA.

Focal Volume Engineering:

Taking into consideration that in LISH microscopy (MP or SP), the lateral resolution of the captured image is determined by the detection optics, independent of the illumination NA; and for MP, the signal is proportional to I^n, it would be possible to engineer the spatial extent of the focal volume of the illumination light so that it is optimized for a particular sample.

For example, an anisotropic NA could be used for the illumination to obtain more uniform signal profile in a scattering sample, effectively increasing the depth penetration. Referring to FIG. 2A, for a particular sample, a particular NA_z is used along the z-axis for the excitation, to meet whatever specification for axial resolution that is needed. If sheet illumination is used the NA along the x-direction would be NA_x~0, and if standard line illumination is used NA_x=NA_z. Because of the scattering in the sample, and assuming that the center of the focal volume is significantly inside the sample, the light intensity has decreased significantly at the focal center, decreasing the signal contrast and thus also the excitation depth penetration.

This scenario can be mitigated by using NA_x>NA_z. The stronger lateral focusing takes light energy away from the right side part of the sample, where the illumination first penetrates the sample, and put it more to the left towards the focal center, increasing the signal contrast in this deeper region, hence improving the signal uniformity over the entire sample and increasing the depth penetration. The larger NA_x illuminates more of the sample laterally away from the focal center, but does not degrade the detected lateral resolution, since that is solely determined by the detection optics. And, by increasing only NA_x, leaving NA_z unchanged, in trying to get more signal at the larger depth, the optimal axial (z) resolution may be maintained.

Anisotropic NA could also be done with NA_x<NA_z, to have less peak excitation intensity, to reduce supra-quadratic photodamage. In general, lower NA_x reduces supra-quadratic photodamage, but increases total light energy imparted onto sample (i.e. increases linear 1 photon photodamage) and reduces signal rate as described earlier.

It will be understood that the above described anisotropic illumination NA could be produced by in any suitable way, such as, for example, two sequential, adjustable slit apertures, oriented 90 degree to each other; and beam expanders that expand each dimension independently, using cylindrical lenses. Another implementation of focal volume engineering could use a Bessel beam. The benefit of a Bessel beam compared to conventional Gaussian beam includes a larger field of view for the same sheet thickness at the center. Bessel beams would be of particular advantage for MP excitation, since the side lobes of a Bessel profile, normally a problem in imaging with 1p excitation, would produce significantly less signal because of the nonlinear dependence of the signal on the intensity. In yet another alternative, focal volume engineering could be implemented with spatial light modulators such as, for example, liquid crystal spatial light modulator, or digital micromirror device, etc.

Advantages of MP-LISH

As will be discussed in the examples that follow, regardless of the specific techniques used, MP-LISH provides superior resolution and mitigates the detrimental effects of scattering/refraction of the excitation light are concerned over SP-LISH microscopy. The longer illumination wavelengths means less scattering, which, in turn, means the light sheet degrades less, preserving resolution at depth. Moreover, even with a degraded light sheet, because of the I^n dependence of the signal in MP-LISH, the degraded part of the light sheet will yield negligible signal The bulk of the signal would come from where the illumination intensity is high, i.e. approximately the same focal volume as if without the degradation. This serves to again preserve the resolution, and make the signal more uniform. Because of the above points, the effective excitation penetration depth is also larger in MP-LISH than SP-LISH.

In addition to these advantages, MP-LISH allows for imaging of a sample with less excitation exposure for the sample, and that in combination with the longer illumination wavelengths, leads to less phototoxicity. In discussing phototoxicity, it is useful to classify the phototoxicity effects into three categories: linear, quadratic, and supra-quadratic, which corresponds to effects that come from absorption of one, two, and more than two photons, respectively. (If we write phototoxicity $\propto I^m$, with I being the peak intensity of the excitation light, then m=1, 2, and >2, for the linear, quadratic, and supra-quadratic phototoxicity, respectively.) As will be discussed in detail below, one of the benefits of multi-photon-excitation LISH microscopy as compared to conventional 2p RPS microscopy is that it is possible to use lower peak excitation intensity leading to lower supra-quadratic photodamage, and the scanning of the "line excitation" yields a "rest" time for the biological sample again leading to less photodamage.

One general feature of LISH microscopy that makes it less phototoxic, compared to conventional microscopy techniques, is that due to its unique orthogonal illumination, the excitation light irradiates only the focal plane that is being observed. With conventional microscopy techniques, where the excitation and detection are collinear, the irradiated light necessarily passes through the entire sample even as information is collected from only one focal plane. Thus, for imaging of a 3D sample composed of n z-slices, LISH would expose the sample to n times less total light energy than conventional microscopes. Since away from the focal plane, the excitation light intensity would be too weak for any appreciable nonlinear absorption, the single-plane illumination feature mainly reduces the linear phototoxicity effects for MP-LISH. Thus, for 2p excitation with NIR wavelengths, the single-plane illumination would help MP-LISH to have less linear toxicity effect due to water absorption in the NIR range compared to conventional 2p-LSM.

Another feature of MP-LISH that makes it less phototoxic than MP-LSM is the lower excitation focusing NA required for reaching the same resolution. Lower NA means lower peak intensity for the same average excitation power, which means that if the same total 2p fluorescence signal is required, the quadratic phototoxicity effect would be the same, while the super-quadratic effect would be less. There has been mounting experimental evidence (see, Ji, N., Magee, J. C. & Betzig, *Nat. Methods* 5, 197-202 (2008) and references therein, the disclosures of which are incorporated herein by reference) that supra-quadratic phototoxicity is the main mechanism for phototoxicity in nonlinear microscopy of in vivo samples. As the intensity scales with the square of the NA, the factor of 10 reduction in NA of 2p-LISH, giving a factor of 100 reduction in I, should significantly reduce the phototoxicity of 2p-LISH compared to 2p-LSM.

Because of the low phototoxicity of MP-LISH compared to MP-LSM, more laser excitation power could be used in MP-LISH in imaging live biological samples while still staying below a certain phototoxicity threshold, therefore achieving higher signal levels and higher image acquisition speed.

Exemplary Embodiments

The person skilled in the art will recognize that additional embodiments according to the invention are contemplated as being within the scope of the foregoing generic disclosure, and no disclaimer is in any way intended by the foregoing, non-limiting examples.

Experimental Set-Up

FIG. 6A shows the schematic diagram of the main components of an exemplary two-photon light sheet (2p-LISH) microscopy setup. The setup can be broken down to six modules (i) light sources and delivery, (ii) scanning, (iii) illumination, (iv) sample control, (v) detection, and (vi) electronic control.

(i) Light Sources

The light sources consist of a 2-photon laser, an ultrafast Titanium: Sapphire laser (COHERENT CHAMELEON ULTRA II) providing 150-femtosecond pulses of near infrared (NIR) radiation at 80 MHz repetition rate, and the 1-photon laser, an Argon-ion laser (LASOS) providing continuous-wave radiation at 488 nm. The NIR light intensity is controlled by the Pockets cell (PC) and associated electronic driver (Conoptics KLA-80A and MR320). The VIS light intensity is controlled by a manual neutral density filter wheel. ND. Galilean telescopes (not shown) are used in each of the NIR and VIS beam to adjust for the optimal beam sizes for the imaging experiments. Motorized mechanical shutters (MS) allow selection of which laser source to be used. Silver-coated mirrors (M) (Thorlabs), with the high broadband reflectivity over the VIS and NIR range, are used throughout the setup for beam routing. The light paths from the two lasers are combined by a long pass dichroic mirror (DM) (Semrock LP750), and travel collinearly for the rest of the setup.

(ii) Scanning Module

The scanning module consists of a pair of orthogonally-mounted galvanometer scanners (GV) (Cambridge Technology, 6150), and a set of scan lens (SL) (focal length=48 mm) and tube lens (TL-1) (focal length=164.5 mm) (gifts from Zeiss). Commercially available scan and tube lenses should work equally well (Design details for the scanning module could be found in Ji, N., et al., *Nat. Methods* 7, 141-U184, (2010), the disclosure of which is incorporated herein by reference.)

(iii) Illumination Module

After the tube lens the scanned laser beam enters the illumination module. The broadband 50/50 plate beamsplitter (BS) (Edmund Optics) splits the beam into the reflected and transmitted beams of approximately same energy—extra neutral density filters (not shown) are put into the beam paths following the BS as needed to adjust for equal beam energies at the sample. Motorized mechanical shutter (MS-T and MS-R) are placed in each of the transmitted and reflected beam path to allow control of uni- or bi-directional illumination. Following the reflected beam path after BS, the lenses combination of SL and TL-1 image the scanned laser spot at GV to the back focal plane of excitation microscope objective 1 (EO-1) (Olympus LMPL10XIR, NA 0.25). The transmitted beam after BS travels to the other side of the sample chamber (SC) and, via two routing mirrors, enters an identical excitation microscope objective (EO-2). Two additional tube lenses (TL-2 and TL-3), identical to TL-1, are used in a 4f configuration along the transmitted beam path to image the scanned laser spot at GV to the back focal plane of EO-2. The two illumination light beams through EO-1 and EO-2 are aligned to be anti-parallel along the x-axis, with the focus regions slightly overlapping at the sample (S), to effectively double the field of view in the x-direction. Scanning of GV about its x-axis (with period of 1 ms) produces a scanned sheet of light along the xy-plane at the sample. As typical imaging exposure time is in the range of tens to hundreds of ms, the non-homogeneity of the scanned sheet produced by the 1-ms scanning period is negligible. The Dove prism (DP) (Thorlabs), mounted on a stage that allows fine rotational adjustments about its x-axis, facilitates alignment of the scanned laser beam through EO-2 so that it is parallel to that through EO-1, along the xy-plane. Both EO-1 and EO-2 are mounted on 4-axis (x, y, z, and rotation about y) kinematic mounts for fine positional control of the laser focus regions.

(iv) Sample-Control Module

The sample-control module consists of the custom-made liquid-filled sample chamber, which has two cover glass windows along the paths of the illumination beams, and a water-tight coupling to the water immersion detection objective. The sample chamber is open at the top, which allows the sample to be mounted to and controlled from above by a combination of motorized positional stages (not shown) that control motion in x, y, z, and rotation about y-axis (Sutter Instrument, Physik Instrumentte, Newport). The sample is mounted with the aid of glass capillaries, following the same general principles as described in Keller, P. J., et al., *Science* 322, 1065-1069 (2008), the disclosure of which is incorporated herein by reference. Details on the preparation and mounting of the specific samples are found in the section below.

(v) Detection Module

The detection module consists of the detection objective (DO) (Zeiss W PLAN APOCHROMAT, 20×, I.ONA) and tube lens (TL-4) (Zeiss, f=164.5 mm), which image the signal contrast at the sample onto the electron-multiplying charged-coupled-device camera (EM-CCD) (Andor DU885) for digital recording, or the eyepieces (EP) for visual observation. The tube lens, switching mirror, eyepieces, and port for EMCCD are all parts of a standard Zeiss microscope headstage. Appropriate optical fillers (F) (Semrock SP750, BP525/50, BP390/12) are used to eliminate the excitation radiation and select for the desired signals. For all the results reported, an additional 0.63× demagnification adapter (Diagnostic Instruments, Inc.) was used after TL-4, to increase the field of view captured by the camera.

(vi) Electronic Control Module

The electronic control module (not shown) is centrally managed by a personal computer (Dell Workstation690) equipped with data acquisition cards (National. Instruments, PCI-6110, PCI-6711). Control of the galvanometer scanning and Pockets cell is handled by the software ScanImage while control of the camera and positional stages are handled by the software Micro-Manager. Z-stack imaging of the sample is done by moving the sample in the z-direction across the light sheet.

Sample Preparations

All animals are raised and handled according to the guidelines of the California Institute of Technology.

(i) *Drosophila*

His2AV-GFP *Drosophila* line, with a strong GFP labeling of the cell nuclei, was obtained from the Bloomington Stock Center. Embryos were collected at 25° C., staged and dechlorinate by bleach using standard procedures. (See, Supatto, W., et al., *Nature Protocols* 4, 1397-1412 (2009), the disclosure of which is incorporated herein by reference.) For LISH imaging, heptane glue was used to cement embryos at the surface of a 0.5-mm glass capillary tube (VWR). Embryos were placed with anterior-posterior axis along the long length of the capillary, and properly oriented so that the side to be imaged from would be facing away from the capillary, allowing direct optical access to the detection objective lens. The embryos-mounted capillary was subsequently transferred into the water-filled sample chamber and held from the top with a pipette holder (Warner Instrument). For imaging with 2p-LSM, embryos were mounted as described in, and imaging was done with the Zeiss 510 Inverted LSM microscope. Sample temperature was kept at 22° C. during imaging. All imaged *Drosophila* embryos were kept for observation after the imaging, and were found to develop normally and hatched within the expected time window.

For the long-term imaging phototoxicity test, typically about ten embryos, all time-staged to be at the same development stage, were mounted on the same capillary. One of the embryos was then selected to undergo the illumination and imaging procedure as described in the main text. The rest of the embryos were inspected on the capillary and a determination was made that the imaged embryo hatched within the same time window as the others. For each imaged embryos (N=6), the resulting approximately 18-hour 3D time-lapse was inspected to verify that the development of the embryo has proceeded normally, as indicated by stereotypical morphogenetic events, lack of increase cell deaths, normal geometry of the cell nuclei, and normal muscle contractions during the last few hours of development.

(ii) Zebrafish

Figure 10:
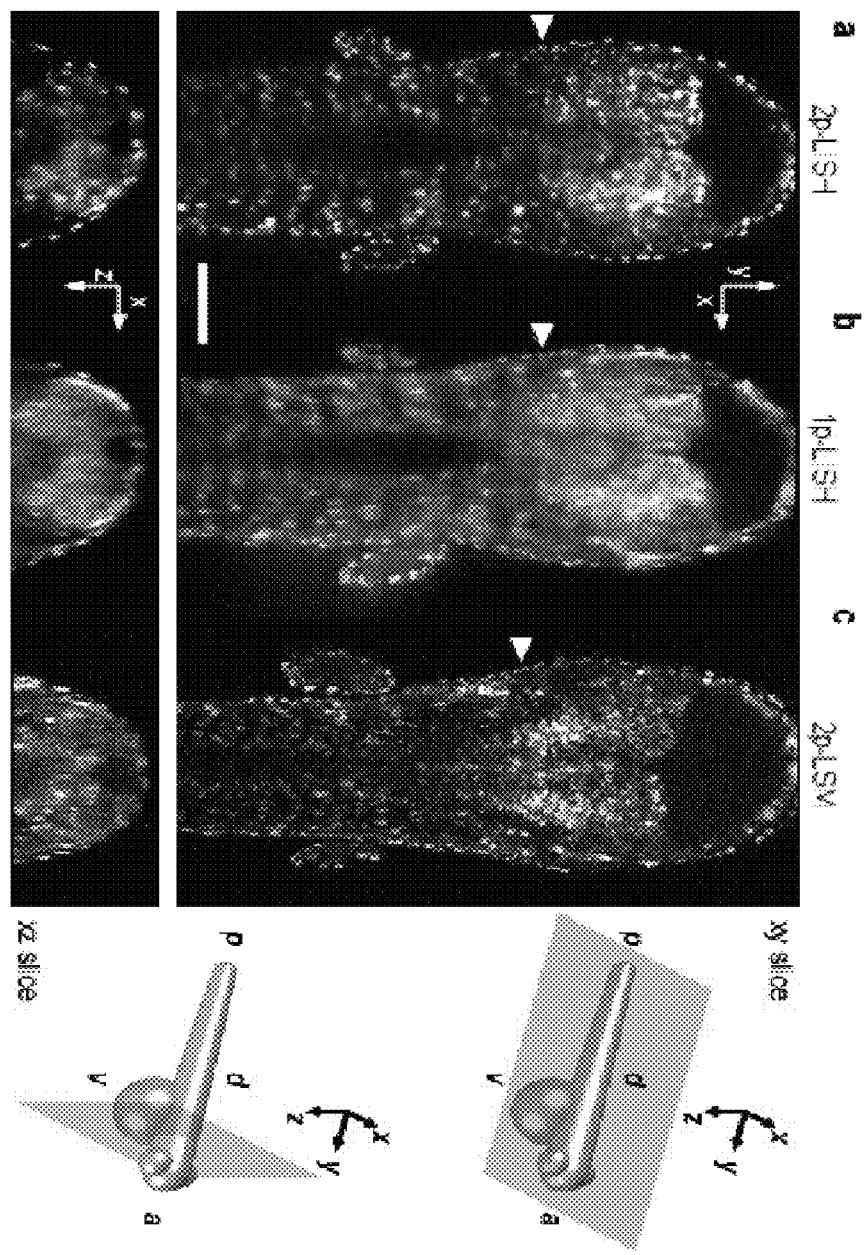
FIGS. 10A to 10C provide images and data comparing the image depth penetration in 45 hpf H2A-Cerulean zebrafish embryos imaged with 2p-LISH (A), 1p-LISH (B), and 2p-LSM (C), where the scale bar=100 µm.

For the data shown in FIG. 10, wild-type zebrafish embryos were injected at the 1-cell stage with 50 ng/μl of H2B-Cerulean mRNA, to ubiquitously label all cell nuclei with Cerulean. For the data shown in FIG. 11, the transgenic zebrafish line (Tg(flk 1-EGFP)) was used. The embryos were then raised in a low salt embryo media (INSTANT OCEAN) as per established procedures until the appropriate time for imaging. Phenylthiourea (PTU) were added to the embryonic raising medium at ~1-somite stage to block pigmentation, making the embryos more transparent for imaging. For LISH imaging, the embryos immersed in liquid 1% solution of low-melt agarose and 30% Danieau (temperature about 35 degree C.), with 0.075% Tricaine as an anesthesia. The embryos were then pulled into 0.85 mm-diameter capillaries. After the agarose solidified (about 1-2 minutes), the capillaries were transferred to the sample chamber, which was filled with the 30% Danieau solution. To prevent movement of the embryos, 0.075% Tricaine was added to both the agarose solution and sample chamber. For conventional 2p-LSM, the same type of agarose solution and sample chamber liquid medium were used to mount the embryos dorsally in standard petri dishes, and imaging was done with the Zeiss 510 Upright LSM microscope. Sample temperature was kept at 24° C. All imaged zebrafish embryos were subsequently freed from the agarose, put back into embryo media, followed through 5 days post fertilization, and were found to develop normally.
(iii) Mouse Tail The tip of the mouse tail was isolated from freshly sacrificed mouse (wild type, young adult) following standard procedure, then skinned, and submerged in fresh 4% PFA made in 1×PBS. The sample was subsequently fixed at room temperature for 6 hours, then washed 6 times with PBS. It was then stained in the dark in 75 nM DAPI in PBS for 1 hour at room temperature, and washed repeated with PBS until use. For imaging, the tail sample was placed directly into the opening of a capillary with inner diameter of 0.85 mm (VWR), and immersed in the sample chamber filled with PBS. In the SHG-LISH imaging of the mouse tail shown in FIG. 12 of the main text, circular polarization was used for the excitation, and no polarization discrimination for the detection.

Experimental Methods

In the following examples, comparisons are made between the performance of the inventive 2p-LISH, 1p-LISH and 2p-LSM. In comparing the imaging performance of the three imaging modalities of 2p-LISH, 1p-LISH, and 2p-LSM, the necessary imaging parameters were first adjusted so that all three modalities achieved the same resolution in imaging an ideal sample of sub-diffraction fluorescent beads (diameter=170 um, Molecular Probes) embedded in clear 1% agarose/water gel.

In taking these baseline studies, 2p-LISH and 1p-LISH were carried out with the light sheet imaging setup described above, while the 2p-LSM was carried out with either an inverted or upright commercial laser scanning microscope (Zeiss 510 NLO) equipped with a COHERENT CHAMELEON ULTRA 2 pulsed laser for 2p excitation. The same microscope objective used in the detection for 2p- and 1p-LISH (Zeiss PLAN APOCHROMAT 20×1.0 NA) was used in 2p-LSM for both illumination and detection. The wavelength for 2p (1p) excitation was 940 (488) nm, and the fluorescence signal centered around 520 nm. Illumination NA was adjusted by adjusting the laser beam size at the back focal plane of the illumination objective lenses, while detection NA was controlled by sub-aperturing the detection optical pathway. With these adjustments, it was possible to achieve the same initial resolution for the three modalities, as shown in FIG. 6B.

In determining the resolution of each technique there are several optical characteristics unique to the different methods that must be taken into account. For example, because in LISH microscopy the illumination and detection optical paths are separate, we have the scenario where the lateral resolution is determined by the detection optics alone, while the axial resolution is determined by both the thickness of the illuminating light sheet and the detection optics. The thinnest of the light sheet is the key in providing the axial sectioning in LISH—as the sheet becomes thicker, the imaging is reduced to conventional wide-field imaging with its inherent lack of axial sectioning due to the blurring effect of out-of-focus light. The focusing property of the illumination light could be well approximated by paraxial Gaussian beam optics. Accordingly, referring to FIG. 6A and its inset, the intensity profile of the beam is described by:

$$I(r, x) = \frac{2P}{\pi w^2} e^{-2r^2/w^2} \quad [\text{EQ. 5}]$$

where P is the total laser power, r is the radial dimension in the yz-plane, x is the propagation direction of the illumination beam (defined to be zero at the focal point), and the beam waist parameter w is given by:

$$w(x) = w_0 \left[1 + \left(\frac{\lambda x}{n\pi w_0^2}\right)^2\right]^{1/2} \quad [\text{EQ. 6}]$$

where $$w_0 = \frac{\lambda}{\pi(NA)} \quad [\text{EQ. 7}]$$

and $$FWHM = \sqrt{2\ln 2} \cdot w_0 \quad [\text{EQ. 8}]$$

with λ being the light wavelength in vacuum, n the medium refractive index, NA the focusing numerical aperture (NA≡n sin θ, where θ is the half focusing angle), $\omega_0$ is the ($e^{-2}$) radius of the beam profile at the focal point, and the full width half maximum (FWHM) of the beam profile is often used to designate the minimum lateral size that a diffraction-limited focused beam of light can reach.

In LISH microscopy, the lateral FWHM of the illumination focus, together with the detection objective lens axial point spread function, determines the axial resolution (along the z-direction) of the final image captured by the camera. The field of view (FOV) of LISH is defined as the extent in the x-dimension about the focal point where the thickness of the light sheet remains below a certain threshold, ensuring that the imaging axial resolution is approximately uniform over the FOV. If this thickness threshold is taken as $\sqrt{2} \cdot w_0$, then the FOV is equal to b, the confocal parameter of the illumination focus:

$$b = \frac{2\pi n \omega_o^2}{\lambda} = \frac{2n\lambda}{\pi(NA)^2} \quad [\text{EQ. 9}]$$

The fluorescence signal rate of 1p-LISH is proportional to the illumination light intensity, $S_{1p} \propto 1$, and hence has the same FWHM, thus the fluorescence light sheet of 1p-LISH has thickness:

$$FWHM_{1p} = \frac{\sqrt{2\ln 2} \cdot \lambda_{1,p}}{\pi(NA_{1p})} \quad [\text{EQ. 10}]$$

The fluorescence signal rate of 2p-LISH is proportional to the squared of the illumination light intensity:

$$S_{2p} \propto I^2 \propto \frac{4P^2}{\pi^2 w^4} e^{-2r^2}/\left(w/\sqrt{2}\right)^2 \quad [\text{EQ. 11}]$$

Thus the radial spatial profile of $S_{2p}$ is also a Gaussian but with the intrinsic width reduced by a factor of $\sqrt{2}$ compared to that of the illumination profile. Then the fluorescence light sheet of 2p-LISH has thickness:

$$FWHM_{2p} = \frac{\sqrt{\ln 2} \cdot \lambda_{2p}}{\pi(NA_{2p})} \quad [\text{EQ. 12}]$$

Since the illumination wavelength in 2p- is about 2 times that in 1p-LISH, $\lambda_{2p} \cong 2 \cdot \lambda_{1p}$, if the same axial resolution is desired with the two modalities, i.e. the same FWHM in EQs. (10) and (12), then we have to use $\sqrt{2}$ times larger NA for 2p-LISH, $NA_{2p} \cong \sqrt{2} \cdot NA_{1p}$. (Note that for $FWHW_{2p} = FWHW_{1p}$ then the FOV EQ. (9) is the same for the two modalities.) The finite variation of the light sheet thickness across the FOV leads to a spatial variation in the average signal: the ratio of the average signal at the center versus at the edge is 2 and 4, for 1p- and 2p-LISH, respectively. This variation, which is usually well accommodated by the high dynamic range of CCD cameras, needs to be taken into account in any quantitative analysis of the captured image.

Neglecting the finite size of the beads, the resolution for each imaging modality was found by analyzing the 3D image of the beads following standard procedures, the disclosure of which is incorporated herein by reference, yielding the FWHM values as follow: 2p-LISH: $\Delta x, y=1.3\pm 0.20$ µm, $\Delta z=1.0\pm 0.33$ µm; 1p-LISH: $\Delta x, y=1.2\pm 0.16$ µm, $\Delta z=2.20\pm 0.30$ µm; 2p-LSM: $\Delta x, y=0.89\pm 0.13$ µm, $\Delta z=1.8\pm 0.25$ µm. To reach these resolution parameters, the NA used in 2p and 1p-LISH were estimated to be ~0.08 and 0.06, respectively, yielding a fluorescence light sheet with FWHM of ~3 µm (EQs. (10) & (12)), and a bidirectional field of view of 2b~250 um (EQ. (9)).

The observed lateral resolutions of all three imaging modalities were determined by the pixel sampling size, rather than optically. For 2p and 1p-LISH, with a 20× detection lens coupled with a 0.63× adapter, the 8-µm camera pixel size corresponds to a pixel size of 0.635 µm at the sample plane, which would yield an effective imaging resolution of 2×0.635=1.27 µm (according to the Nyquist criterion), which was approximately what we observed. For 2p-LSM, the point-scanning pixel size was set at 0.29 µm, which would yield an effective resolution of 0.58 µm, approximately what was observed. The observed axial resolutions of all three imaging modalities was larger than what was expected optically from the NA=1.0 of the objective lens used, as expected since the full NA was not utilized due to significant sub-aperturing.

For 2p-LSM, to reach an axial resolution $\Delta z=2$ µm, the same as experimentally reached in 2p-LISH, requires a focusing NA of 0.83 (see Zipfel, W. R., et al., *Nat. Biotechnol* 21, 1369-1377 (2003), the disclosures of which is incorporated herein by reference.). Thus, it can be seen that to reach approximately the same axial resolution of 2 µm, 2p-LISH uses a focusing NA that is smaller compared to that used in 2p-LSM by: 0.83/0.08~10 fold.

Example 1

Depth Penetration/Resolution of MP-LISH
(*Drosophila* Internal Structures)

With this same initial resolution performance, the three modalities were then compared in imaging live embryos, to see how deep into the scattering sample the resolution and image quality could be maintained, using fluorescently-labeled cell nuclei as test objects. Since the nuclei had size of ~5 um, for the imaging modalities the initial resolution of ~1 um laterally and ~2 um axially was chosen.

Figure 7:
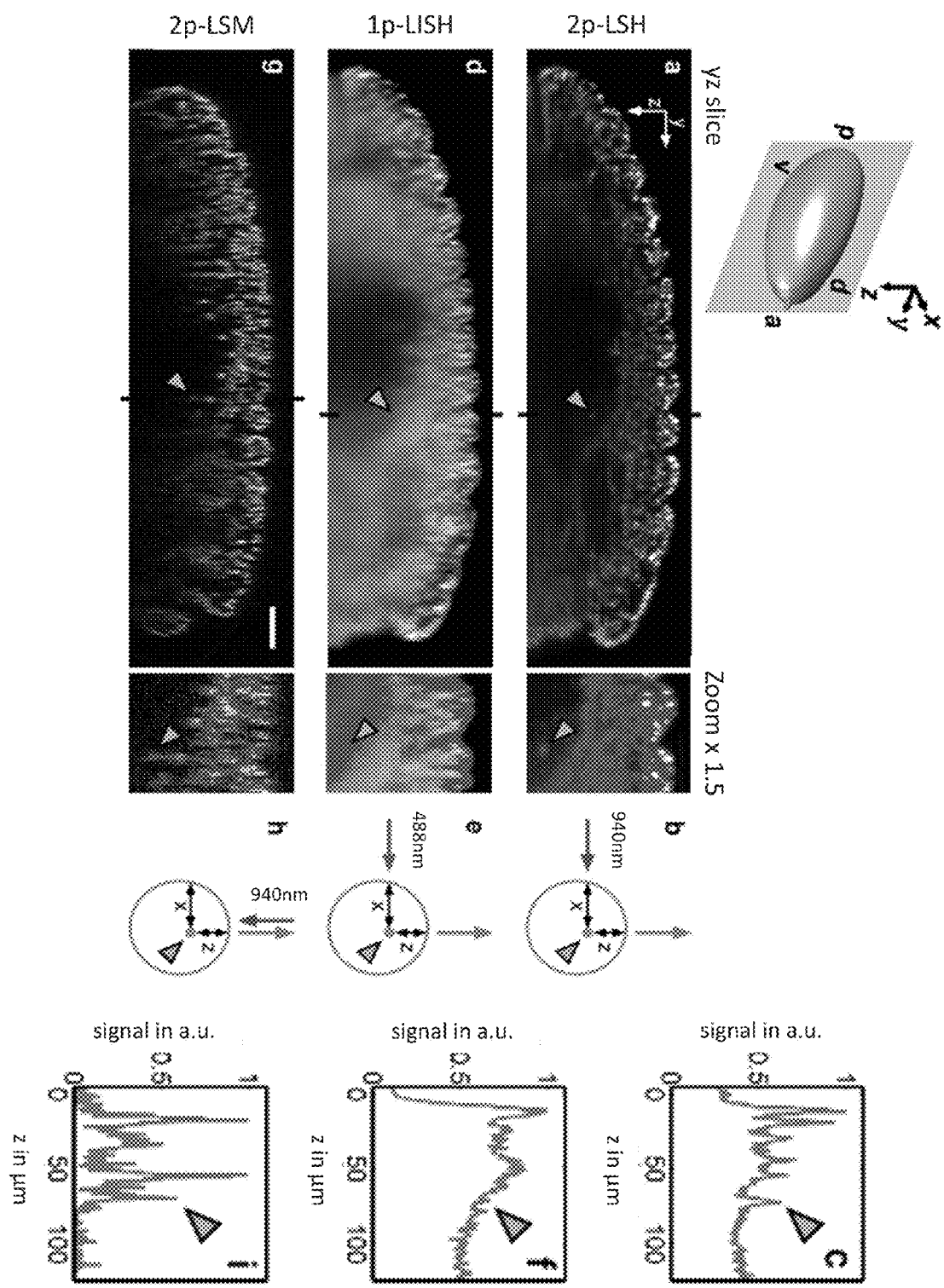
FIGS. 7A to 7I provide images and data comparing image depth penetration in stage 13 H2A-GFP *Drosophila* embryos imaged with 2p-LISH (A-C), 1p-LISH (D-F), and 2p-LSM (G-I), where the scale bar=50 µm.

To demonstrate the ability of 2p-LISH to maintain good signal contrast and spatial resolution deep inside biological samples, it was compared to 1p-LISH and 2p-LSM in imaging the internal cells of live, *Drosophila* embryos at stage 13 (FIG. 7). (In this data, FIGS. 7A, D & G provide yz-slices comparing the cellular resolution of a deep cell (gray arrow), FIGS. 7B, E & H provide the position with this deep cell (gray arrows) is indicated (x~100 µm and z~70 µm) with the embryo viewed from the anterior side, showing the excitation (arrows) and the detection (arrows) optical directions, and FIGS. 7C, F & I provide a signal profile along a y-line (indicated between black bracket in FIGS. 7A, 7D & 7G).) The same embryo was imaged using 2p-LISH and 1p-LISH with the lateral side facing the detection objective and the light sheet along the xy-plane entering the embryos from ventral side. Similarly-staged embryo was imaged in 2p-LSM with the lateral side facing the excitation/detection objective a: anterior, p: posterior, d: dorsal, v: ventral, where the scale bar=50 µm.

Generally for optical imaging techniques, the depth penetration is described by the distance into a sample at which scattering and aberration effects have spatially degraded the image quality beyond a required resolution. The axial resolution is usually degraded much faster than the lateral resolution as a function of depth. Thus, the depth performance of optical imaging techniques is best assessed by analyzing axial slices (xz- or yz-plane) of 3D data stacks, as shown in FIG. 7.

Comparing FIG. 7A-C and 7D-F a dramatic increase in depth penetration of 2p-LISH over 1p-LISH can be observed. While the cellular resolution, especially axially, of the 1p-LISH image is quickly lost for increasing depth into the embryo (both in the excitation and detection direction, corresponding to x- and z-axis, respectively), the 2p-LISH images show cellular resolution at least twice deeper inside the embryo (gray arrows in FIG. 7A-F). Since both 2p- and 1p-LISH use the same wide-field imaging detection, the improved depth penetration of 2p-LISH must result from the use of NIR nonlinear excitation.

There are three factors that contribute to this increased resolution: (i) lower level of background in the 2p-LISH image due to the reduced biological auto-fluorescence associated with usage of NIR excitation wavelengths; (ii) longer wavelength NIR light scatters much less than VIS light, hence for 2p-LISH the light sheet thickness spatially degrades less at large depth into biological tissue, preserving axial resolution; (iii) the quadratic dependence of the fluorescence signal on the excitation light intensity for the nonlinear two-photon process acts to spatially confine the generated signal only to the thin high intensity part of the light sheet, maintaining resolution even for a spatially degraded sheet. This last feature, importantly, allows bidirectional illumination in 2p-LISH to be carried out simultaneously, since the spatially degraded part of the light sheet from one side does not have enough peak intensity to create fluorescence signal to blur out the signal from the non-degraded part of the light sheet coming from the other side of the sample. This is in contrast with 1p-LISH, where bidirectional illumination has to be done sequentially, and the final image reconstructed computationally, because linear excitation allows significant background to be created by the degraded part of the light sheet. (See, Huisken, J., et al., *Science* 305, 1007-1009 (2004) and Holekamp, T. F., et al., *Neuron* 57, 661-672, (2008), the disclosures of each of which are incorporated herein by reference.) (For images presented in all figures, 2p-LISH data were taken with simultaneous bidirectional illumination, while 1p-LISH data were taken with sequential bidirectional illumination and reconstructed computationally.) Comparing FIGS. 7A-C and 7G-I, the depth penetration of 2p-LSM and 2p-LISH appear comparable.

Example 2

Depth Penetration/Resolution of MP-LISH
(*Drosophila* External Structures)

Figure 8:
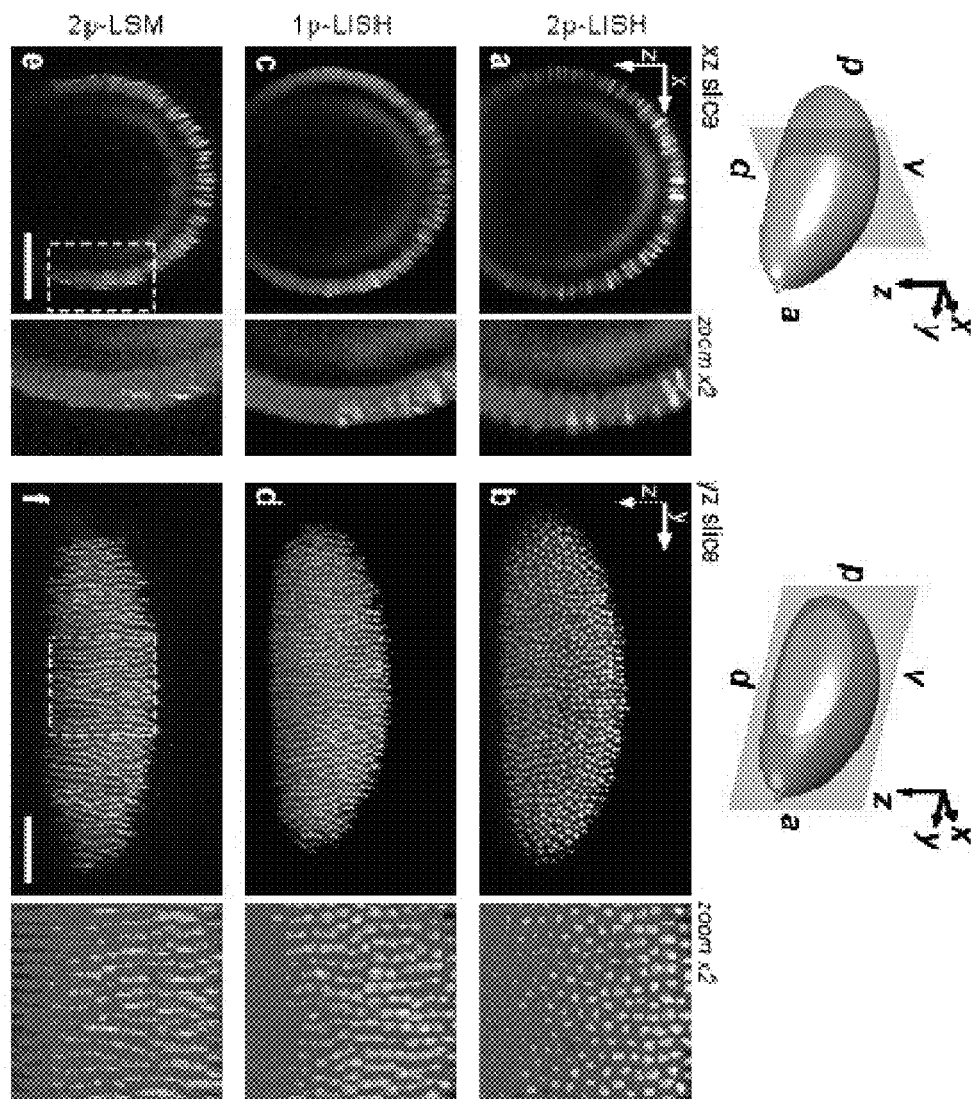
FIGS. 8A to 8F provide images and data comparing the image axial resolution in stage 5 H2A-GFP *Drosophila* embryos imaged with 2p-LISH (A-B), 1p-LISH (C-D), and 2p-LSM (E-F), where the scale bar=50 µm.

In addition to the nonlinear excitation, the use of low NA focusing also contributes to the optimized depth penetration of 2p-LISH. This is demonstrated by imaging *Drosophila* before gastrulation, when all of the cell nuclei are regularly distributed along the surface of the embryo, providing an ideal model for testing the resolution around, rather than into, a biological object (FIG. 8).

As expected, good spatial resolution is observed in all three techniques when imaging the tissue surface close to the detection objective (ventral side of the embryo: upper part in FIGS. 8A, C, and E). However, on the lateral sides of the embryos (see yz-slices FIGS. 8B, D and F), much improved axial resolution of 2p-LISH is seen compared to the other two techniques. While the cell nuclei can be resolved almost all-around the embryo in 2p-LISH (FIG. 8A-B), they appear elongated in the z-direction and smeared together on the lateral sides in 1p-LISH (FIG. 8C-D) or 2p-LSM (FIGS. 8E-F).

Figure 9:
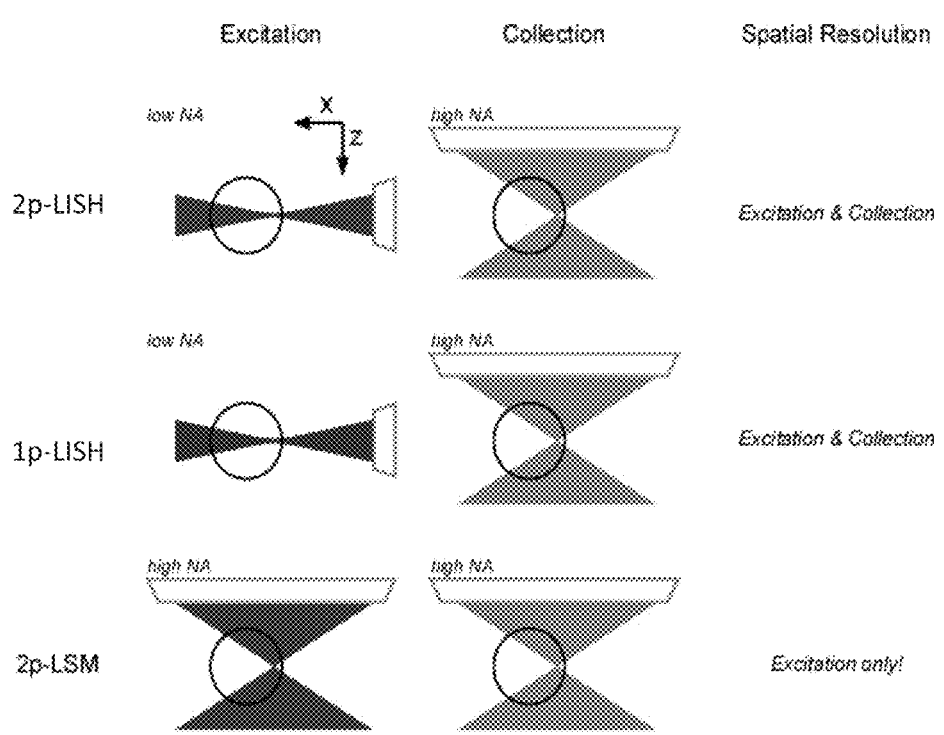
FIG. 9 provides a schematic comparing the excitation and detection optical paths in 2p-LISH, 1p-LISH and 2p-LSM.

Here 2p-LISH outperforms 1p-LISH in depth penetration similarly to FIG. 7, but the improvement in axial resolution of 2p-LISH over 2p-LSM comes directly from the low and high NA focusing, respectively, used in these techniques. In 2p-LSM, the high NA necessarily means that for the region towards the lateral sides of the embryo, approximately half of the focusing solid angle goes through water and the other half goes through the embryo. This is because the same objective is used in 2p-LSM, whereas two different objectives are used in 2p-LISH and 1p-LISH, and whereas in 2p-LSM the spatial resolution depends only on the excitation, both excitation and detection contribute to the spatial resolution in 2p-LISH or 1p-LISH (see FIG. 9). Thus, inhomogeneous scattering loss, coupled with aberrations, would cause the focal volume to be significantly larger than the diffraction limit, leading to the loss of axial resolution as seen in FIGS. 8E-F. In contrast, for 2p-LISH, with the lower NA focusing, the inhomogeneous scattering loss and aberration would be greatly reduced, hence yielding the excellent axial resolution (FIGS. 8A-B). Thus, it has been illustrated that for a 3D biological sample, the low NA focusing of 2p-LISH results in a spatial resolution that is less sensitive to the sample's optical inhomogeneity, compared to techniques using typically 10 fold higher NA (2p-LSM, CLSM, etc.).

Example 3

Depth Penetration/Resolution of MP-LISH (Zebrafish)

The improved resolution performance of 2p-LISH is also demonstrated in imaging live zebrafish (Danio rerio) embryos (FIG. 10). The zebrafish is an important vertebrate animal model that, even though is significantly less optically opaque than *Drosophila*, still presents considerable challenge to 4D imaging, especially at its later stages of embryonic development (beyond the first day after fertilization). (See, Supatto, W., et al., *Nature Protocols* 4, 1397-1412 (2009), the disclosure of which is incorporated herein by reference.) The comparison of the three techniques for imaging 45 hours-post-fertilization (hpf) zebrafish embryos confirms that 2p-LISH achieves higher depth penetration than 1p-LISH (again by at least a factor of 2), resolving cellular structures within the hindbrain and neural tube that 1p-LISH does not (FIGS. 10A and 10B).

In particular, the upper panel shows xy-slices through the image z-stacks at depth of ~130 μm from the dorsal top of the embryos, while lower panel show xz-slices through the embryos at the locations marked by white arrows. All slices shown are maximum intensity projections over a 3-μm thickness of the 3D data sets. 2p-LISH (FIG. 10A) achieved higher depth penetration than 1p-LISH (FIG. 10B), resolving cellular structures within the hindbrain and neural tube that 1p-LISH does not. Comparing (FIG. 10B) and (FIG. 10C) shows that the difference in depth penetration is small between 2p-LISH and 2p-LSM, with 2p-LSM slightly winning out in the denser region of the hindbrain. The same embryo was imaged in 2p-LISH (FIG. 10A) and 1p-LISH (FIG. 10B) with the dorsal side facing the detection objective and the light sheet along the xy-plane entering the embryos from lateral sides. Similar staged embryo was imaged using 2p-LSM (FIG. 10B) with the dorsal side facing the excitation/detection objective (a:anterior, p:posterior, d:dorsal, v:ventral). Comparing FIGS. 10A and 10C, it can be clearly seen that 2p-LISH has close to the depth penetration of 2p-LSM, losing out in the denser region of the hindbrain.

Example 4

Phototoxicity and Acquisition Speed of MP-LISH

An important property of any 4D biological imaging modality is its phototoxicity quality, since the threshold of phototoxicity as a function of excitation power fundamentally limits how much light could be irradiated onto the sample, which ultimately determine how fast the image acquisition speed could be (after considerations for excitation saturation and imaging hardware speed have been optimized). 2p-LISH is expected to be substantially less phototoxicity than conventional 2p-LSM mainly because of the much lower peak laser excitation intensity, resulting from the lower focusing NA of the light sheet geometry (a factor of 10 smaller in NA yields a factor of 100 smaller in intensity). For imaging with 2p excitation, at the typically-used level of average excitation power, lower peak excitation intensity has been shown to reduce phototoxicity and photobleaching by limiting the detrimental supra-quadratic processes that comes from absorption of more than two photons (see SOM for more discussion on phototoxicity). (See, Ji, N., Magee, J. C. & Betzig, E., *Nat. Methods* 5, 197-202 (2008), the disclosure of which is incorporated herein by reference.)

To test the low phototoxic quality of 2p-LISH, the normal development and hatching rate of *Drosophila* embryos submitted to continuous illumination with high average laser power, at illumination conditions that would enable high speed 4D imaging was investigated. Embryos were constantly illuminated from both sides during essentially the entire embryonic development, using total excitation power of 200 mW at 940 nm wavelength at the sample (100 mW from each illumination direction). This excitation power is about 5 times higher than the phototoxicity threshold for these embryos when imaged with conventional 2p-LSM. (See, Supatto, W., (2009), cited above.) The sample was scanned through the light sheet at 10 μm·s$^{-1}$ speed over 190 μm range every 20 s, allowing z-stack image acquisition covering the whole embryo, for up to ~18 hours until the end of the *Drosophila* embryonic development. All embryos survived (N=6), underwent normal timed sequence of development, showed no phenotypic signs of phototoxicity (such as increased cell deaths or disrupted morphogenetic movements), and hatched normally at the end of the time lapse recordings. Photobleaching of the fluorescence labels was negligible, as no significant change in signal was detected. Thus these results experimentally confirmed the lower phototoxicity quality of 2p-LISH compared to 2p-LSM, allowing use of at least 5 fold more average excitation power in long-term 4D imaging of a live biological sample.

The low level of phototoxicity in 2p-LISH, and the resulting higher excitation power that can be used without toxicity effects, permits in vivo 4D imaging at speed and SNR that are unreachable with conventional 2p-LSM. For instance, the 5 fold increase of excitation power used for illuminating *Drosophila* embryos with 2p-LISH described earlier leads to a 2p-excitation fluorescence signal that is $5^2$=25 fold stronger than what can be achieved with conventional 2p-LSM before reaching phototoxicity. Note that excitation saturation is minimized in 2p-LISH due to the 100-fold reduction in excitation intensity used in 2p-LISH compared with 2p-LSM, thus an increase in excitation power should directly translate to an increase in signal These experiments also show this signal is sufficient to acquire a full volume coverage of the entire embryo (250 μm×635 μm×190 μm=30×$10^6$ μm$^3$) in less than 20 s, with high SNR and high spatial sampling (0.635 μm×0.635 μm×1.25 μm voxel size), at speed of 80 ms exposure time for a frame rate of 8 frames per second (fps). At these conditions, the acquisition speed is an order of magnitude faster than what can be achieved with conventional 2p-LSM before the onset of phototoxicity. (See, Supatto, W., (2009), cited above.)

Figure 11:
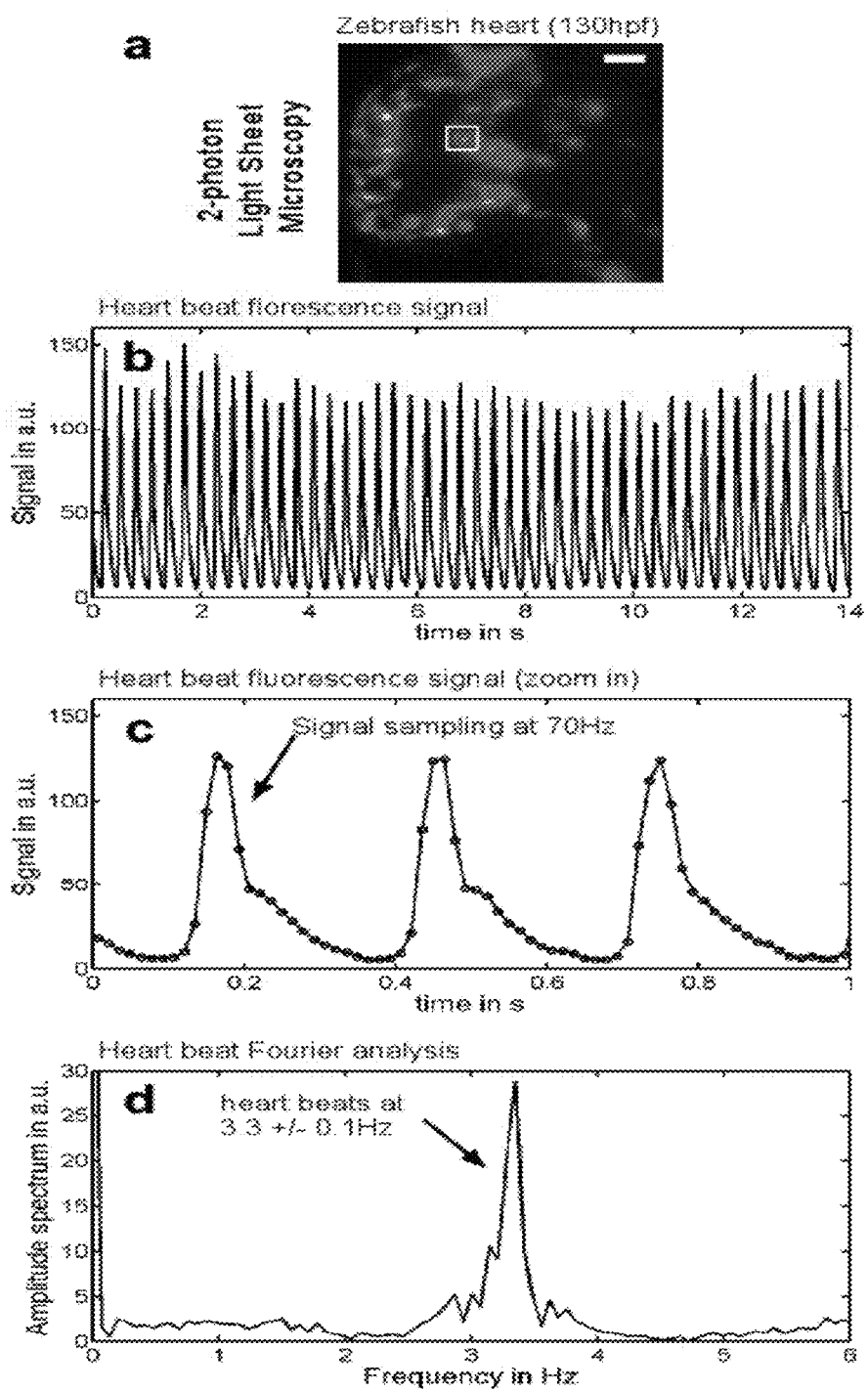
FIGS. 11A to 11D provide images and data of an analysis of a heart beating from high-speed 2p-LISH imaging of a 5.4 day old zebrafish embryo (130 hpf), the fluorescence signal is averaged in a small area of the heart (white square in A) and plotted depending on time (B), the variation of signal during 1 s (C) shows the fast acquisition rate at 70 fps allows capturing fast features during each beat cycle, and the Fourier analysis of the time variation of the fluorescence signal over the 14 s-time interval (D), where the scale bar in a is 20 µm.

2p-LISH is capable of even faster acquisition speed, beyond video rate, as shown in FIG. 11, where the beating heart inside a live late-stage zebrafish embryo (130 hpf) was imaged with cellular resolution at 70 fps, using 50 mW average excitation power, capturing the fast motion of the heart valve leafets, all without any sign of phototoxicity. As shown, the variation of signal during 1 s (FIG. 11C) shows the fast acquisition rate at 70 fps allows capturing fast features during each beat cycle, and the Fourier analysis of the time variation of the fluorescence signal over the 14 s-time interval (FIG. 11D) shows a sharp peak at 3.3 Hz demonstrating a regular heart beating during the entire acquisition period.

Example 5

Second Harmonic Generation Light Sheet Microscopy

A useful feature of a conventional 2p-LSM setup is that it can be used to combine fluorescence with harmonic generation imaging, where image contrast is generated by certain symmetry properties of the biological sample itself, without requiring exogenous labeling. The combination of 2p-LSM with second and third harmonic generation LSM has been recently applied for imaging embryos. (See, Olivier, N. et al., *Science* 329, 967-971, (2010), the disclosure of which is incorporated herein by reference.) The multi-modality of the inventive MP-LISH device has been demonstrated by straightforwardly extending it to second harmonic generation light sheet (SHG-LISH) microscopy. In SHG, where the signal photon has exactly twice the energy (or half the wavelength) of the excitation photon, is generated from the noncentrosymmetry exhibited in various endogenous biological molecules, including many structural components such as collagen. (Campagnola, P. J. & Loew, L. M., *Nat. Biotechnol* 21, 1356-1360, (2003) and Williams, R. M., et al., *Biophys. J.* 88, 1377-1386, (2005), the disclosures of each of which are incorporated herein by reference.)

Figure 12:
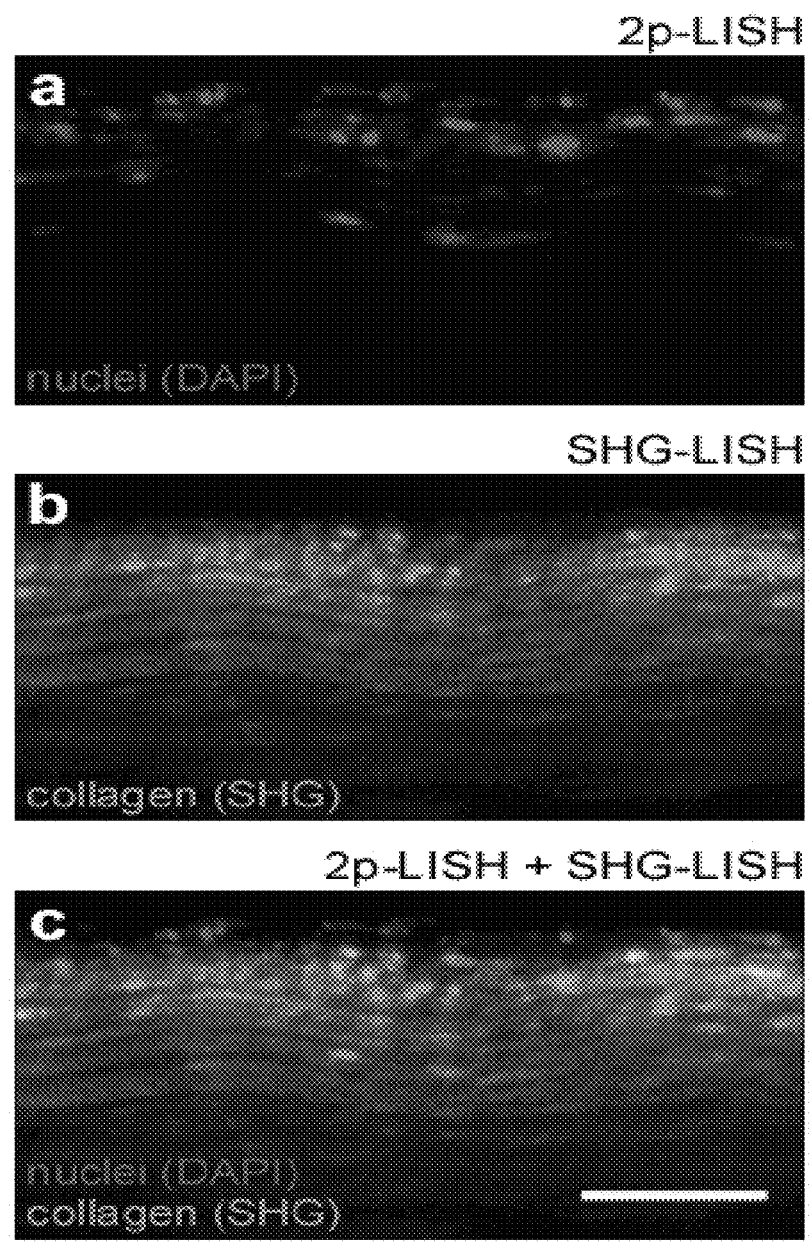
FIGS. 12A and 12B provide images and data of two-photon fluorescence from DAPI-stained nuclei (A), second harmonic generation (SGH) signal from collagen (B) of a mouse tail collected using the same light sheet microscopy setup, and a combined view of the two signals (C), where the scale bar=50 µm.

To demonstrate the effectiveness of a SHG-MP-LISH, a mouse tail tissue was imaged on the same light sheet setup combining two contrast mechanisms: SHG signal from the collagen fibers and 2p-excited fluorescence signal from labeled cell nuclei (FIG. 12). In this embodiment, excitation wavelength was at 798 nm, and the DAPI (SHG) signal was collected with spectral bandpass of 450-520 (389.5-400.5) nm. As shown, the SHG signal is mostly directed toward the illumination optical axis due to coherent mechanisms, though complex arrangements of SHG-active scatterers at the sub-wavelength scale could produce signal directed at substantial angles away from the illumination axis, which would be detected in the light sheet geometry, as demonstrated in FIG. 12. (See, Williams, R. M., et al., (2005), cited above.)

More generally, SHG-LISH appears to be the technique of choice for high-speed imaging of SHG signal that is more isotropically generated, such as in the case of SHG from synthetic nanoprobes. (See, Pantazis, P., et al., *Proceedings of the National Academy of Sciences*, doi:10.1073/pnas.1004748107 and Pu, Y., et al., *Phys. Rev. Lett.* 104, (2010), the disclosures of each of which are incorporated herein by reference.)

SUMMARY OF INVENTION

As has been demonstrated above, the new imaging modality of 2p-LISH achieves an optimized compromise point of both high depth penetration and high imaging speed, without compromising normal biology—a combination that was not possible with existing imaging techniques. Given that the detection of 2p-LISH is subjected to the blurring effect due to scattering of the signal photons by the sample, inherent to all techniques that employ the wide-field imaging detection strategy, it is somewhat surprising that the inventive 2p-LISH performs as well as it does in depth penetration, achieving a two-fold improvement over 1p-LISH and comparable to 2p-LSM. It should be noted that in the above examples the improved depth penetration of 2p-LISH described comes entirely from optimizing the illumination, with utilization of 2p excitation and lower focusing NA. If the wide-field detection is also optimized, such as through deconvolution or non-coherent structured illumination, 2p-LISH should achieve even higher depth penetration. (See, Verveer, P. J. et al., *Nat. Methods* 4, 311-313, (2007); Breuninger, T., et al., *Opt. Lett.* 32, 1938-1940 (2007); and Keller, P. J. et al., *Nat. Methods* 7, (2010), the disclosures of each of which are incorporated herein by reference.)

It has also been demonstrated that the signal rate of 2p-LISH is equal to that of 2p-LSM because the excitation beam is maintained as one single coherent unit, in space and in time. Other strategies that allow parallelized2p-excitation such as multi-focus illumination or pulse splitting divide the beam into distinct units in space or in time, respectively, and thus has an inherently lower signal rate (for the same average power) than 2p-LSM due to the quadratic dependence of the signal on the intensity (See, Ji, N., Magee, J. C. & Betzig, E., *Nat. Methods* 5, 197-202 (2008) and Bewersdorf, J., et al., *Opt. Lett.* 23, 655-657 (1998), the disclosures of each of which are incorporated herein by reference.)

It has also been shown that the scanned sheet implementation helps in achieving the optimized signal rate of 2p-LISH. The intrinsic equal signal rate of 2p-LISH and 2p-LSM then allows any increase in average excitation power used in 2p-LISH to translate directly to higher signal levels, and hence higher acquisition speed. The ability of 2p-LISH to accommodate higher excitation power, due to its lower phototoxicity quality, makes 2p-LISH a fast imaging technique in a fundamental way, beyond just hardware instrumentation. Thus, 2p-LISH is expected to compare favorably against other parallelized mp-excitation imaging modalities in terms of the potential for fast 4D imaging, since 2p-LISH is the only modality with the unique orthogonal geometry of light sheet, with the inherent lower NA focusing, resulting in lower peak excitation, and hence lower phototoxicity. (See, Bewersdorf, J., et al., (1998), cited above.)

As the acquisition speed and SNR of 2p-LISH is increased by using higher average excitation power, the improvement will be eventually limited by the threshold of power where phototoxicity is determined by linear or quadratic (involving absorption of one or two photons) rather than supra-quadratic processes. This threshold power is expected to vary for different biological samples, but general considerations suggests that the threshold for toxic heating effects due to linear absorption by water might lie in the one Watt range (see Schönle, A. & Hell, S. Heating by absorption in the focus of an objective lens. *Opt. Lett.* 23, 325-327 (1998), the disclosure of which are incorporated herein by reference). Consideration of toxic linear heating effects also further illustrates the advantage of using a scanned light sheet, versus a static one, for implementing 2p-LISH. Even though the lower peak intensity of the static sheet reduces supra-quadratic phototoxicity, it requires more than ten times higher average power just to produce the same signal rate as the scanned sheet. This high power requirement would not only be beyond what commercially-available lasers could provide, but also would likely be higher than the threshold for toxic linear heating.

Although many of the capabilities of 2p-LISH have been examined, the technique could be further extended by implementation of recent developments that improve 1p-LISH or 2p-LSM, such as multi-view imaging and reconstruction, multi-angle illumination, focal volume engineering, and adaptive optics. (See, Preibisch, S., et al., *Nat. Methods* 7, 418-419, (2010); Olivier, N., et al., *Opt. Lett.* 34, 1684-1686 (2009); Fahrbach, F. O., et al., *Nat Photon advance online publication, doi*: nphoton.2010.204.html#supplementary-information (2010); and Huisken, J. & Stainier, D. Y. R., *Opt. Lett.* 32, 2608-2610 (2007); Ji, N., Milkie, D. E. & Betzig, E., *Nat. Methods* 7, 141-U184, (2010), the disclosures of each of which are incorporated herein by reference.) With the unique combination of low-NA-focusing, high resolution, high depth penetration, high speed, and multimodality, 2p-LISH is suitable for extensive 4D imaging of live biological sample and is expected to find a wide range of biomedical applications.

Doctrine of Equivalents

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A multi-photon excitation light sheet microscope comprising:
   a sample holder;
   at least one excitation source, said excitation source being capable of producing an excitation beam having a power of adequate intensity to induce significant levels of multi-photon excitation in a sample, and being disposed such that the excitation beam is directed along at least one excitation beam path, wherein the at least one excitation beam path is provided with an excitation focusing optics for producing a substantially two-dimensional multi-photon excitation light sheet that defines a sample excitation region which extends along the excitation beam path and transversely thereto and intersects with at least a portion of the sample holder;
   an imaging detector defining at least one detection beam path and capable of detecting an excitation generated signal contrast from the sample excitation region, the detector being disposed such that the detection direction of the at least one detection beam path is substantially orthogonal to the direction of the excitation beam path; and
   wherein the multi-photon excitation light sheet is comprised of photons that each have an energy such that the sum of the energy of at least two of said photons is sufficient to cause multi-photon excitation and thereby excite a signal contrast in said sample excitation region, and wherein said signal contrast is proportional to $I^n$, where I is the instantaneous intensity of the excitation energy at the sample excitation region and n is the number of said at least two photons that cause multi-photon excitation.

2. The microscope as claimed in claim 1, wherein the number of photons that cause multi-photon excitation light sheet is two.

3. The microscope as claimed in claim 1, wherein the excitation source is a pulsed near-infrared laser selected from the group consisting of lasers having pulse duration in the nanosecond, picosecond, and femtosecond range.

4. The microscope as claimed in claim 1, wherein the detected excitation generated signal contrast is selected from the group consisting of fluorescence, second harmonic generation, third harmonic generation, sum frequency generation, and stimulated Raman scattering.

5. The microscope as claimed in claim 1, wherein the excitation focusing optics comprises a spherical lens through which the excitation beam is focused, and wherein the excitation beam is laterally scanned along a desired axis of the excitation beam to form the light sheet, said light sheet having an effectively uniform excitation intensity across said excitation region.

6. The microscope as claimed in claim 1, wherein the excitation focusing optics comprises a cylindrical lens, and wherein the sample excitation region is created by statically focusing the excitation beam through said cylindrical lens.

7. The microscope as claimed in claim 1, wherein the at least one excitation source is capable of creating two coaxial and oppositely aligned excitation beams, such that said sample excitation region is formed from the non-coherent adjoining of the excitation regions created by each of the excitation beams.

8. The microscope as claimed in claim 1, wherein the numerical aperture of the excitation focusing optics is adjustable.

9. The microscope as claimed in claim 8, wherein the adjustable numerical aperture comprises a beam expander with an adjustable expanding ratio.

10. The microscope as claimed in claim 1, wherein focal volume engineering is applied to the excitation beam to optimize for light sheet imaging.

11. The microscope as claimed in claim 10, wherein focal volume engineering is implemented using one of the techniques selected from the group consisting of having the numerical aperture of the excitation focusing optics being anisotropic along at least two axes of said excitation beam, and having the excitation beam be a Bessel beam.

12. The microscope as claimed in claim 10, wherein the focal engineering is implemented by one or more optical elements selected from the group consisting of two orthogonally oriented sequential adjustable slit apertures, a plurality of independently expanding beam expanders, liquid crystal spatial light modulators, digital micromirror device spatial light modulators, and axiconic lens.

13. The microscope as claimed in claim 1, wherein the sample holder is moveable relative to the sample excitation region along or about at least one axis.

14. The microscope as claimed in claim 1, wherein the sample excitation region is moveable relative to the sample holder along or about at least one axis.

15. The microscope as claimed in claim 1, wherein the sample excitation region is one of either substantially planar-shaped or linearly-shaped.

16. A method of imaging an object using a multi-photon excitation light sheet microscope comprising:
    producing a multi-photon excitation beam, and directing said excitation beam along an excitation beam path;
    focusing said excitation beam to produce a substantially two-dimensional multi-photon excitation light sheet that defines a sample excitation region, said sample excitation region being disposed to extend along the excitation beam path and transversely thereto;
    placing a sample within said sample excitation region to generate a signal contrast;
    detecting said signal contrast along a detection beam path that is substantially orthogonal to the excitation beam path; and
    wherein the multi-photon excitation light sheet has sufficient excitation intensity to produce significant levels of multi-photon excitation, the energy of said photons being selected such that cumulatively sufficient excitation energy is provided to excite a signal contrast in said sample excitation region, and wherein said signal contrast is proportional to $I^n$, where I is the instantaneous intensity of the excitation energy at the sample excitation region and n is the number of photons involved in the multi-photon excitation.

17. The method as claimed in claim 16, wherein producing the excitation beam includes using a pulsed near-infrared laser selected from the group consisting of lasers having pulse durations in the nanosecond, picoseconds, and femtosecond range.

18. The method as claimed in claim 16, wherein detecting the signal contrast includes using a detection technique selected from the group consisting of 2-photon-excited fluorescence, second harmonic generation, third harmonic generation, sum frequency generation, and stimulated Raman scattering.

19. The method as claimed in claim 16, wherein the signal contrast comes from molecules and structures endogenous to a biological sample.

20. The method as claimed in claim 16, wherein the signal contrast comes from exogenous labels that are introduced into a biological sample.

21. The method as claimed in claim 16, wherein the signal contrast is second harmonic generation coming from nano-sized probes which have been introduced into a biological sample.

22. The method as claimed in claim 16, further comprising spherically focusing and laterally scanning said excitation beam along a desired axis of the excitation beam path to form the light sheet such that said light sheet has an effectively uniform excitation intensity across said excitation region.

23. The method as claimed in claim 16, further comprising forming at least two coaxial and oppositely aligned excitation beams, such that said sample excitation region is formed from the non-coherent adjoining of the excitation regions created by each of the said excitation beams.

24. The method as claimed in claim 16, wherein the focusing of the excitation beam further includes adjusting the numerical aperture of a focusing optic.

25. The method as claimed in claim 16, wherein the focusing of the excitation beam further includes anisotropically adjusting the numerical aperture of a focusing optic such that the excitation beam is anisotropic along at least two axes.

26. The method as claimed in claim 16, wherein the imaging is performed in one of either a 3D or 4D mode.

\* \* \* \* \*

UNITED STATES PATENT AND TRADEMARK OFFICE
CERTIFICATE OF CORRECTION

PATENT NO. : 8,441,633 B2
APPLICATION NO. : 12/915921
DATED : May 14, 2013
INVENTOR(S) : Thai V. Truong et al.

Page 1 of 1

It is certified that error appears in the above-identified patent and that said Letters Patent is hereby corrected as shown below:

In the Claims

In claim 2, column 26, lines 21-22, delete "light sheet".

Signed and Sealed this
Sixteenth Day of July, 2013

Teresa Stanek Rea
*Acting Director of the United States Patent and Trademark Office*